United States Patent
Patsenker et al.

(10) Patent No.: US 9,034,655 B2
(45) Date of Patent: May 19, 2015

(54) HIGHLY WATER-SOLUBLE, CATIONIC LUMINESCENT LABELS

(75) Inventors: Leonid D. Patsenker, Kharkov (UA); Inna G. Yermolenko, Kharkov (UA); Iryna A. Fedyunyaeva, Kharkov (UA); Yelena N. Obukhova, Kharkov (UA); Olga N. Semenova, Kharkov (UA); Ewald A. Terpetschnig, Urbana, IL (US)

(73) Assignee: SETA BioMedicals, LLC, Urbana, IL (US)

( * ) Notice: Subject to any disclaimer, the term of this patent is extended or adjusted under 35 U.S.C. 154(b) by 767 days.

(21) Appl. No.: 12/906,893

(22) Filed: Oct. 18, 2010

(65) Prior Publication Data

US 2011/0143387 A1 Jun. 16, 2011

Related U.S. Application Data

(63) Continuation-in-part of application No. 11/820,508, filed on Jun. 19, 2007, now abandoned.

(60) Provisional application No. 60/814,972, filed on Jun. 19, 2006.

(51) Int. Cl.
*C07D 239/70* (2006.01)
*C07D 403/12* (2006.01)
(Continued)

(52) U.S. Cl.
CPC ............ *C07D 403/12* (2013.01); *C07D 209/60* (2013.01); *C07D 219/02* (2013.01);
(Continued)

(58) Field of Classification Search
CPC .. C07D 403/12; C07D 209/60; C07D 219/02; C07D 221/14; C07D 239/74; C07D 285/14; C07D 307/77; C07D 413/14; C07D 471/04; C07D 471/06; C07D 471/14; C09K 2211/1007; C09K 2211/1011; C09K 2211/1014; C09K 2211/1029; C09K 2211/1033; C09K 2211/1044; C09K 2211/1048

USPC ............................................. 436/164; 435/29
See application file for complete search history.

(56) References Cited

U.S. PATENT DOCUMENTS

2003/0235846 A1* 12/2003 Terpetschnig et al. ............ 435/6

OTHER PUBLICATIONS

Patsenker, et al., "Formation and Destruction of Diazine Ring under Conditions of the Vilsmeier-Haack Formylation of 4-Dialkylaminonaphthalic Acid Derivatives," Tetrahedron (2000) 56, 7319-7323.

(Continued)

*Primary Examiner* — Rebecca M Fritchman
(74) *Attorney, Agent, or Firm* — DASCENZO Intellectual Property Law, P.C.

(57) ABSTRACT

Luminescent labels based on aromatic and heterocyclic compounds, including reactive intermediates used to synthesize these compounds, and methods of synthesizing and using these reporter compounds. These labels combine high photostabilities, large Stokes' shifts and contain a pyrimidinium moiety as a water-soluble group. These luminescent compounds relate generally to the following structure:

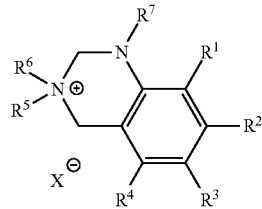

The methods relate generally to the synthesis and/or use of reporter compounds for fluorescence lifetime or fluorescence polarization based applications.

24 Claims, 5 Drawing Sheets

(51) Int. Cl.
*C07D 209/60* (2006.01)
*C07D 219/02* (2006.01)
*C07D 221/14* (2006.01)
*C07D 239/74* (2006.01)
*C07D 285/14* (2006.01)
*C07D 307/77* (2006.01)
*C07D 413/14* (2006.01)
*C07D 471/04* (2006.01)
*C07D 471/06* (2006.01)
*C07D 471/14* (2006.01)
*C09K 11/06* (2006.01)
*C12Q 1/02* (2006.01)

(52) U.S. Cl.
CPC ............ *C07D221/14* (2013.01); *C07D 239/74* (2013.01); *C07D 285/14* (2013.01); *C07D 307/77* (2013.01); *C07D 413/14* (2013.01); *C07D 471/04* (2013.01); *C07D 471/06* (2013.01); *C07D 471/14* (2013.01); *C09K 11/06* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1048* (2013.01)

(56) References Cited

OTHER PUBLICATIONS

Patsenker, et al., "Formation and Cleavage of the Quinazolinium Ring in Vilsmeier-Haack Formylation of 4-Dialkylamino-Substituted Naphthalic Acid Derivatives," Chem. Heterocycl. Comp. (2000) 36:5, 611-612.

Patsenker, et al., "Heterocyclization in Vilsmeier-Haack Formylation of Dimethylamino-Substituted 2,5-Diaryloxazoles and 2,5-Diaryl-1,3,4- Oxadiazoles," Chem. Heterocycl. Comp. (2000) 36:5, 623-625.

Lyubenko, et al., "Dimethyamino-Substituted 7H-Benzo[*de*]pyrazolo[5,1-α]isoquinolin-7-ones and Their Behavior Under Vilsmeier-Haack Conditions," Chem. Heterocycl. Comp. (2003) 39:4, 511-519.

Patsenker, et al., "The Behavior of Dimethylamino-Substituted 2,5-Diaryloxazoles and 2,5-Diaryl-1,3,4-Oxadiazoles Under Vilsmeier-Haack Conditions," Chem. Heterocycl. Comp. (2003) 39:4, 525-533.

Semenova, et al., "New data on the "t-Amino effect" in series of 4-R-N,N-dimethylanilines," Func. Mat. (2003) 10:4, 730-737.

\* cited by examiner

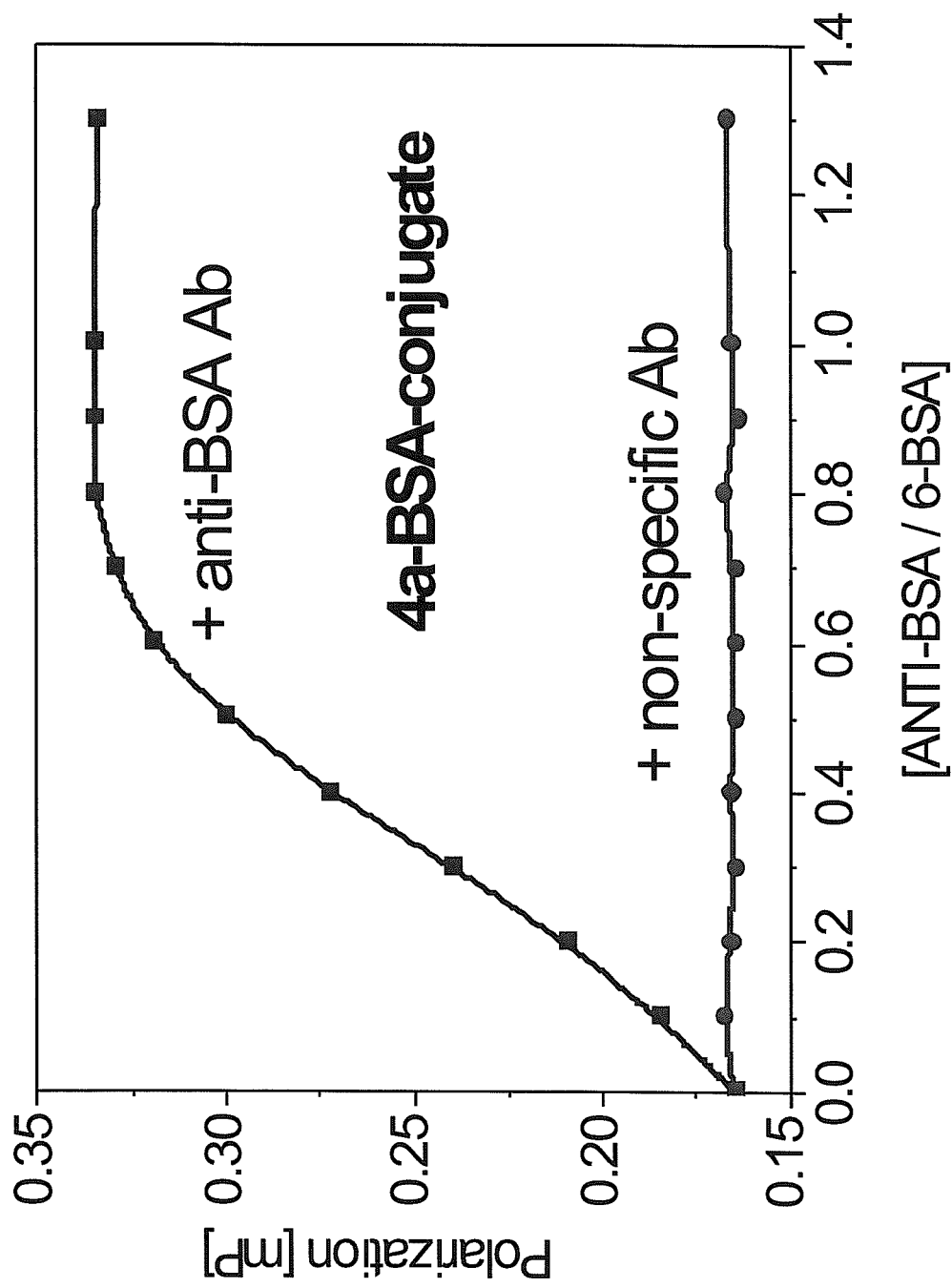

HIGHLY WATER-SOLUBLE, CATIONIC LUMINESCENT LABELS

CROSS-REFERENCES TO RELATED MATERIALS

This application is a continuation-in-part under 35 U.S.C. §120 of application Ser. No. 11/820,508 filed on Jun. 19, 2007, now abandoned hereby incorporated by reference, which in turn is based upon and claims the benefit under 35 U.S.C. §119(e) of U.S. Provisional Patent Application Ser. No. 60/814,972, filed Jun. 19, 2006. This application further incorporates by reference in their entirety for all purposes all patents, patent applications (published, pending, and/or abandoned), and other patent and nonpatent references cited anywhere in this application. The cross-referenced materials include but are not limited to the following publications: Richard P. Haugland, HANDBOOK OF FLUORESCENT PROBES AND RESEARCH CHEMICALS (6$^{th}$ ed. 1996); JOSEPH R. LAKOWICZ, PRINCIPLES OF FLUORESCENCE SPECTROSCOPY (2$^{nd}$ Ed. 1999); RICHARD J. LEWIS, SR., HAWLEY'S CONDENSED CHEMICAL DICTIONARY (12$^{th}$ ed. 1993).

TECHNICAL FIELD

The invention relates to compounds based on heterocyclic compounds among others. More particularly, the invention relates to compounds based on cationic heterocyclic compounds among others that are useful as labels and luminescent reporters, in particular for lifetime- and fluorescence polarization-based applications.

BACKGROUND

Luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a colorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. A luminescence lifetime is the average time that a luminophore spends in the excited state prior to returning to the ground state. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTS) and charge-coupled devices (CODs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit detection of emission light without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminophore also may have a luminescent lifetime (FLT) that is similar to that of the autoluminescence of biological and other samples; such autoluminescence is particularly significant at wavelengths below about 600 nm. The luminophore also may be expensive, especially if it is difficult to manufacture.

SUMMARY

The invention provides luminescent labels based on aromatic and heterocyclic compounds, among others, reactive intermediates used to synthesize these compounds, and methods of synthesizing and using these reporter compounds, among others. These labels combine high photostabilities, large Stokes' shifts and contain a cationic pyrimidinium moiety as the water-soluble group. These luminescent compounds relate generally to the following structure:

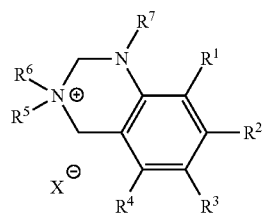

wherein each $R^1$-$R^4$ is independently selected from the group consisting of H, alkyl, halogen, sulfo, carboxy, formyl, acetyl, formylmethyl, sulfate, phosphate, ammonium, cyano, nitro, azido, heterocyclic, substituted heterocyclic, reactive aliphatic, aromatic and reactive aromatic groups, among others and $R^5$, $R^6$ and $R^7$ are selected from alkyl, aryl and reactive alkyl;

adjacent substituents $(R^1, R^2)$, $(R^2, R^3)$, $(R^3, R^4)$, $(R^1, R^2, R^3)$ or $(R^2, R^3, R^4)$ together with interspersed atoms may form an aromatic or heterocyclic ring system that is further substituted; adjacent substituents $(R^5, R^6)$ may also form a cyclic system.

The methods relate generally to the synthesis and/or use of reporter compounds for fluorescence lifetime or fluorescence polarization based applications especially those described above.

The nature of the invention will be understood more readily after consideration of the drawings, chemical structures, and detailed description that follow.

ABBREVIATIONS

Figure 1:
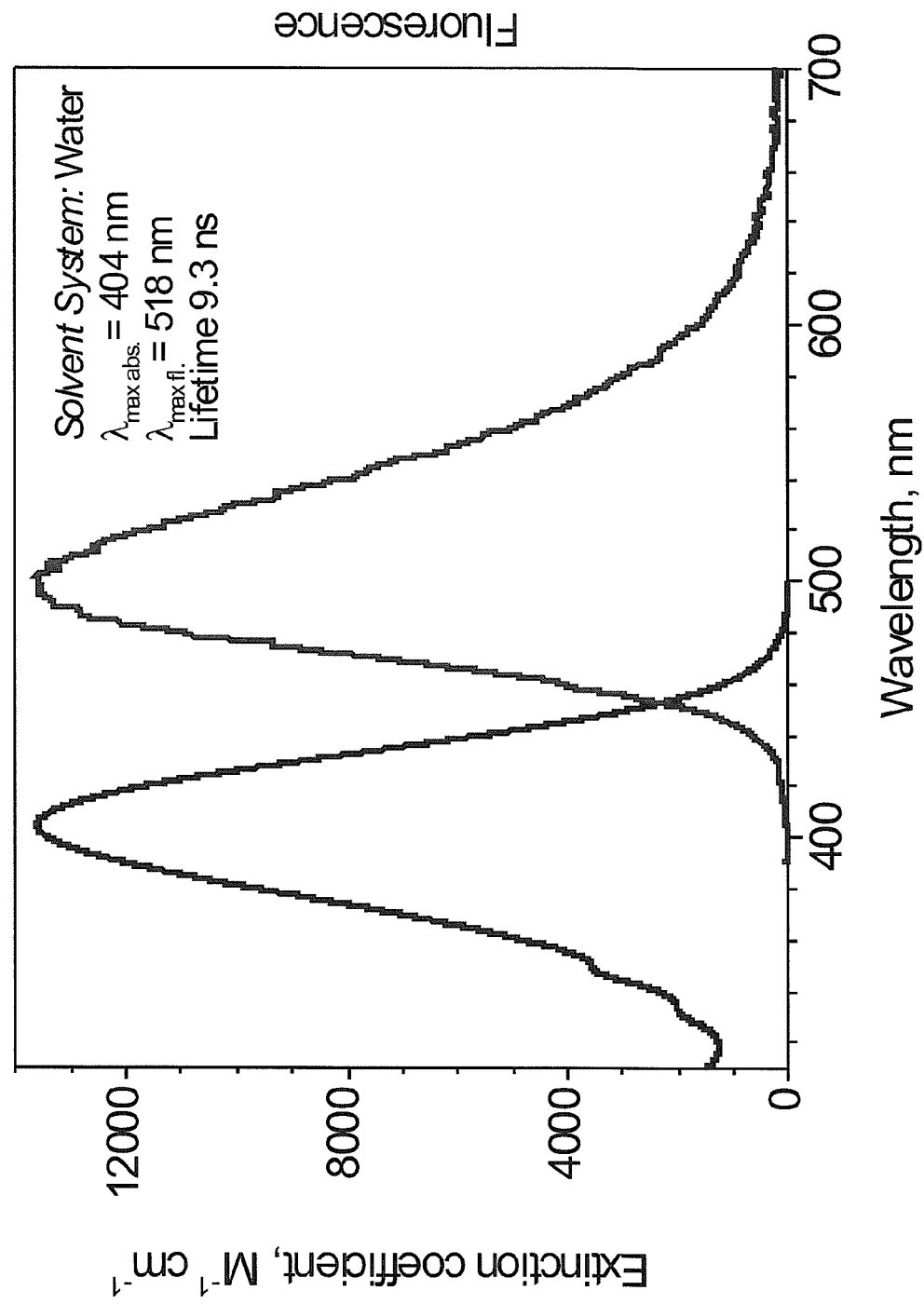
FIG. 1. shows the absorption and emission spectra of compound 3 in water.
Figure 2:
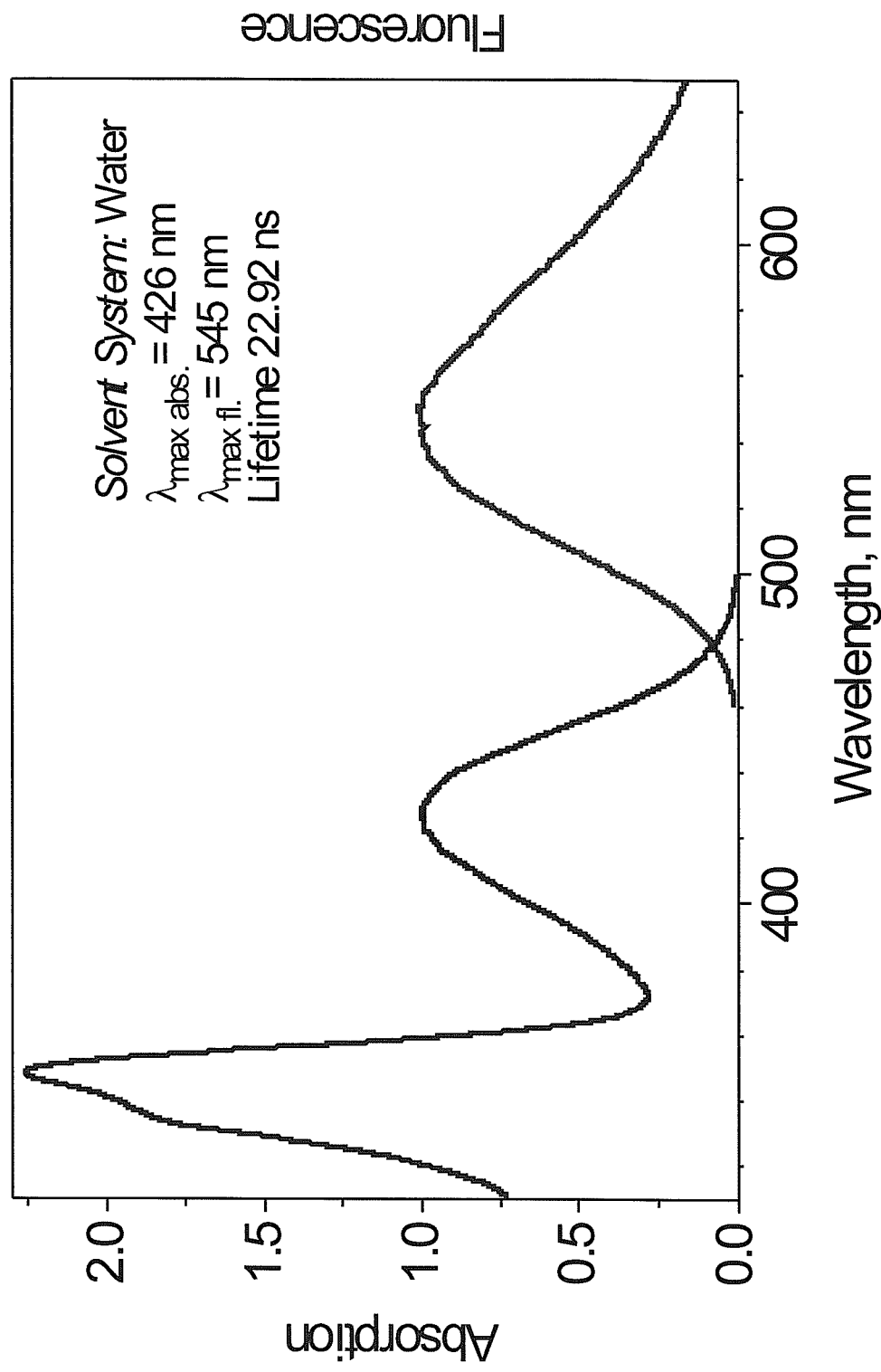
FIG. 2. shows the absorption and emission spectra of compound 6 in water.
Figure 3:
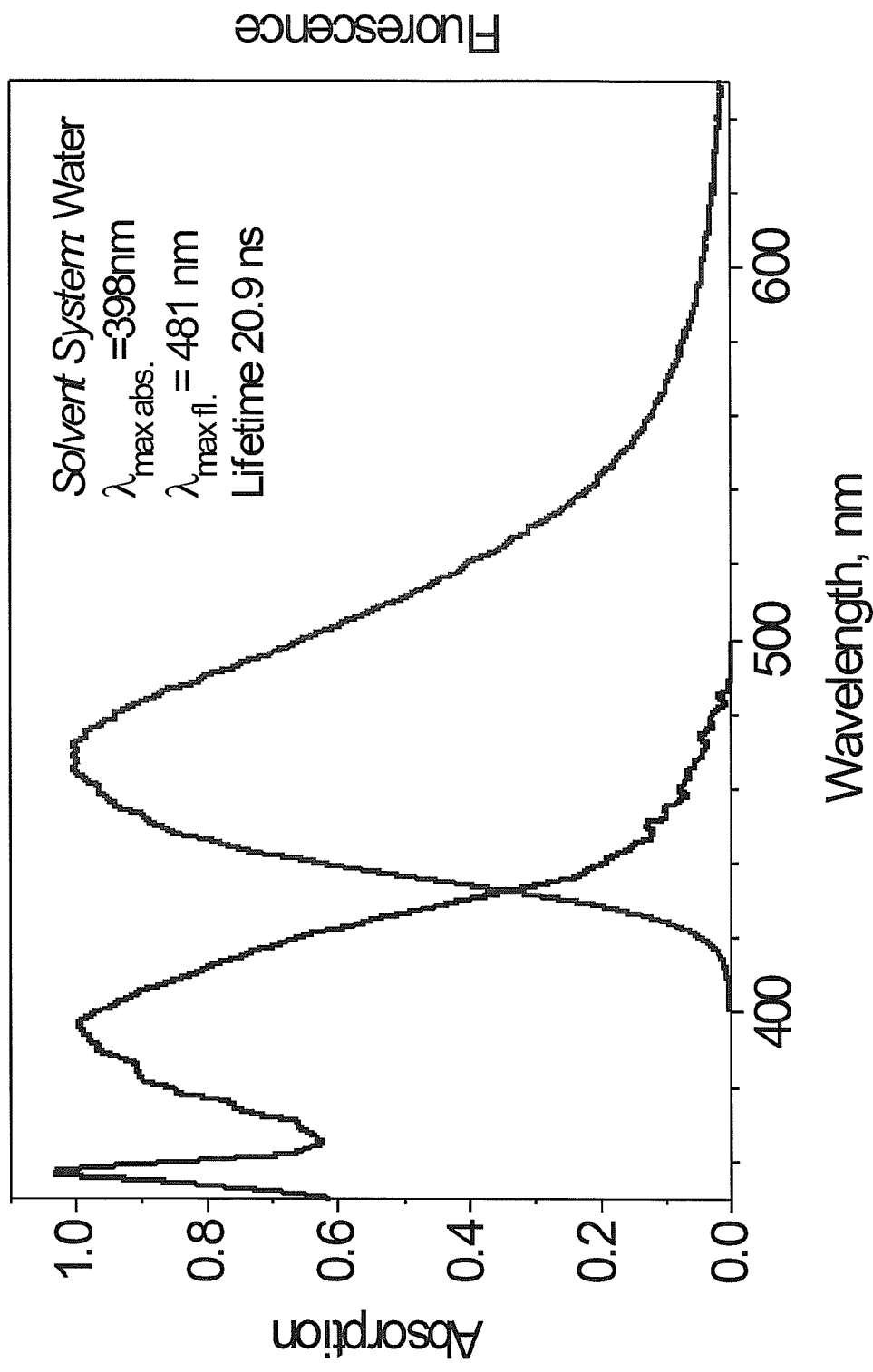
FIG. 3. shows the absorption and emission spectra of compound 13 in water.

The following abbreviations, among others, may be used in this application.

| Abbreviation | Definition |
| --- | --- |
| abs | Absorption |
| BSA | bovine serum albumin |
| Bu | butyl |
| DCC | dicyclohexylcarbodiimide |
| DIPEA | N,N-diisopropylethylamine |
| DMF | dimethylformamide |
| DMSO | dimethylsulfoxide |
| D/P | dye-to-protein ratio |
| Et | ethyl |
| fl | fluorescence |
| FLT | fluorescence lifetime |
| g | grams |
| h | hours |
| HSA | human serum albumin |
| L | liters |
| Lit. | Literature |
| m | milli ($10^{-3}$) |
| M | molar |
| MM | Molecular Mass |
| Me | methyl |
| mol | moles |
| M.P. | melting point |
| n | nano ($10^{-9}$) |
| ns | Nanosecond(s) |
| NHS | N-hydroxysuccinimide |
| NIR | near infrared region |
| PB | Phosphate buffer |
| Ph | Phenyl |
| ps | Picosecond(s) |
| Prop | Propyl |
| Q.Y. | Quantum Yield |

| Abbreviation | Definition |
| --- | --- |
| TSTU | O-(N-succinimidyl)-N,N,N',N'-tetramethyluronium tetrafluoroborate |
| s | Second(s) |
| $\lambda_{max}$ (abs) | absorption maximum |
| $\lambda_{max}$ (fl) | emission maximum |
| $\mu$ | micro ($10^{-6}$) |

DETAILED DESCRIPTION OF THE INVENTION

The invention relates generally to luminescent compounds containing a benzo-pyrimidinium moiety as a water-soluble functionality having luminescent lifetimes in the order of a few ns or higher and their synthetic precursors, and to methods of synthesizing and using such compounds. These luminescent compounds may be useful in both their free and conjugated forms, as probes or labels. This usefulness may reflect in part enhancement of one or more of the following: fluorescence lifetime, fluorescence polarization, quantum yield, Stokes' shift, and photostability.

The remaining discussion includes (1) an overview of structures, (2) an overview of the synthetic methods, and (3) a series of illustrative examples.

Overview of Structures

The luminescent reporter compounds may be generally described by the following structure:

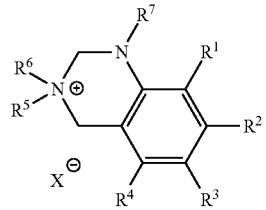

wherein each $R^1$-$R^4$ is independently selected from the group consisting of H, alkyl, alkoxy, amino, alkylamino, dialkylamino, alkenyl, alkinyl, aryl, halogen, sulfo, carboxy, formyl, acetyl, formylmethyl, sulfate, phosphate, phosphonate, ammonium, alkylammonium, cyano, nitro, azido, heterocyclic, aromatic, reactive aliphatic and reactive aromatic groups and wherein at least one pair of adjacent substituents $(R^1, R^2)$, $(R^2, R^3)$, $(R^3, R^4)$, together with interspersed atoms forms an aromatic or heterocyclic ring system that is further substituted and $R^1$-$R^3$ are alkyl and reactive alkyl -L-$R^x$.

The substituents on the substituted rings may be chosen quite broadly, and may include the various components listed below, among others.

Cationic Reporters

The main structural feature of these luminescent labels is the benzo-pyrimidinium moiety which impairs water-solubility on these compounds, without the need of introducing additional solubilizing groups such as sulfo- or phosphonate groups, which can sometime be a tedious effort.

The influence of the pyrimidinium-function on the fluorescence properties (Q.Y. and lifetime) can be better understood by comparing Compound 1 (the precursor of Compound 5) and Compound 5 (containing the pyrimidinium moiety) in the same solvent system (ethanol):

| Dye # | Structure | Solvent | QY [%] | Lifetime [ns] |
|---|---|---|---|---|
| 1 | (structure: N,N-dimethylamino naphthalimide, N-phenyl) | Ethanol | 0.5 | <<1 |
| 5 | (structure: pyrimidinium-substituted naphthalimide, N-phenyl, Cl⁻ counterion) | Ethanol | 58 | 8.5 |
|   |   | Water | 75 | 9.4 |

While the lifetime of Compound 1 in ethanol is extremely short (<<1 ns), the lifetime of the pyrimidinium compound in ethanol was measured to be in the order of 9.4 ns. It is worth mentioning that the lifetime and Q.Y. of compound 1 are even further reduced in water. The favorable spectral and photophysical properties of these pyrimidinium based compounds were the reason for us to utilize them as labels for biomolecules in aqueous environments. There are several features of these compounds that make them very useful as biological labels:

The pyrimidinium moiety carries a positive charge that helps to maintain the net charge of a protein, e.g. when the ε-amino group in proteins is reacted with an NHS ester or reactive group to an amide bond. The positive charge of the fluorophore helps to compensate for the loss of the at neutral pH positively-charged ε-amino group. This is in particular important for gel electrophoresis, a procedure which enables the sorting of molecules based on size and charge. One approach to visualize these molecules is by labeling a small number of them with a reactive fluorescent dye, which should not change the net charge of the molecule.

Compounds of this invention also exhibit large Stokes' shifts which is advantageous when such compounds are used as biological labels. It is known that upon covalent attachment of several dyes onto one biomolecule the quantum yield or fluorescence lifetime of these dyes will be reduced in particular if the Stokes' shift is small. As an example the lifetime of compound 3 in water is 9.3 ns and labeled to IgG at a D/P ratio of about 1 the lifetime is 8.9 ns. Even at very high D/P ratios of about 8 the lifetime is still 8.4 ns (Table 1), a 10% overall decrease in fluorescence lifetime. As a comparison, fluorescent labels such as fluorescein-isothiocyanate (FITC) ($\tau$=4.0 ns) exhibit lifetime losses of up to 40% or more when covalently labeled to proteins at similar D/P ratios (D/P~8) e.g. see J. R. Lakowicz et al., Biopolymers 74(6): 467-475 (2004).

We also found that the fluorescent lifetimes of these labels are much longer than conventional fluorophores for them to enable measurement of high molecular-weight analytes in a fluorescence polarization assay (FIG. 5).

The Stokes' shifts are very important in fluorescence polarization measurements where too small Stokes shifts lead to high degree of homo-energy transfer between dyes thereby reducing the polarization. Importantly the Stokes' shifts of the fluorescent labels of this invention are in the order of at least 50 nm but more typical 80-100 nm.

As described below these compounds are in particular useful for fluorescence lifetime and fluorescence polarization based applications and methods.

Reactive Groups ($R^x$).

The substituents on these compounds may include one or more reactive groups, where a reactive group generally is a group capable of forming a covalent attachment with another molecule or substrate. Such other molecules or substrates may include proteins, carbohydrates, nucleic acids, and plastics, among others. Reactive groups ($R^x$) vary in their specificity, and may preferentially react with particular functional groups and molecule types. Thus, reactive compounds generally include reactive groups chosen preferentially to react with functional groups found on the molecule or substrate with which the reactive compound is intended to react.

The compounds of the invention are optionally substituted, either directly or via a substituent, by one or more chemically reactive functional groups that may be useful for covalently attaching the compound to a desired substance. Each reactive group $R^x$ may be bound to the compound directly by a single covalent bond (—$R^x$), or may be attached via a covalent spacer or linkage, -L-, and may be depicted as -L-$R^x$.

The reactive group (—$R^x$) of the invention may be selected from the following functional groups, among others: activated carboxylic esters, acyl azides, acyl halides, acyl halides, acyl nitriles, acyl nitriles, aldehydes, ketones, alkyl halides, alkyl sulfonates, anhydrides, aryl halides, azindines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

The following reactive functional groups (—$R^x$), among others, are particularly useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;
b) Iodoacetamides and maleimides, which form covalent bonds with thiol-functions, as in proteins;
c) Carboxyl functions and various derivatives, including N-hydroxybenztriazole esters, thioesters, p-nitrophenyl esters, alkyl, alkenyl, alkynyl, and aromatic esters, and acyl imidazoles;
d) Alkylhalides, including iodoacetamides and chloroacetamides;
e) Hydroxyl groups, which can be converted into esters, ethers, and aldehydes;
f) Aldehydes and ketones and various derivatives, including hydrazones, oximes, and semicarbozones;
g) Isocyanates, which may react with amines;
h) Activated C=C double-bond-containing groups, which may react in a Diels-Alder reaction to form stable ring systems under mild conditions;
i) Thiol groups, which may form disulfide bonds and react with alkylhalides (such as iodoacetamide);
j) Alkenes, which can undergo a Michael addition with thiols, e.g., maleimide reactions with thiols;
k) Phosphoramidites, which can be used for direct labeling of nucleosides, nucleotides, and oligonucleotides, including primers on solid or semi-solid supports;

l) Primary amines that may be coupled to variety of groups including carboxyl, aldehydes, ketones, and acid chlorides, among others; and
m) Boronic acid derivatives that may react with sugars.
n) Azides and alkynes that are used in click-chemistry approaches R Groups The R moieties associated with the various substituents of Z may include any of a number of groups, as described above, including but not limited to aliphatic groups, alicyclic groups, aromatic groups, and heterocyclic rings, as well as substituted versions thereof.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

As used herein, "alicyclic groups" include hydrocarbon substituents that incorporate closed rings. Alicyclic substituents may include rings in boat conformations, chair conformations, or resemble bird cages. Most alicyclic groups are derived from petroleum or coal tar, and many can be synthesized by various methods. Alicyclic groups may optionally include heteroalicyclic groups, that include one or more heteroatoms, typically nitrogen, oxygen, or sulfur. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aromatic groups may include groups of unsaturated cyclic hydrocarbons containing one or more rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Any substituent of the compounds of the invention, including any aliphatic, alicyclic, or aromatic group, may be further substituted one or more times by any of a variety of substituents, including without limitation, F, Cl, Br, I, carboxylic acid, sulfonic acid, CN, nitro, hydroxy, phosphate, phosphonate, sulfate, cyano, azido, amine, alkyl, alkoxy, trialkylammonium or aryl. Aliphatic residues can incorporate up to six heteroatoms selected from N, O, S. Alkyl substituents include hydrocarbon chains having 1-22 carbons, more typically having 1-6 carbons, sometimes called "lower alkyl".

As described in WO01/11370, sulfonamide groups such as $—(CH_2)_n—SO_2—NH—SO_2—R$, $—(CH_2)_n—CONN—SO_2—R$, $—(CH_2)_n—SO_2—NH—CO—R$, and $—(CH_2)_n—SO_2NH—SO_3H$, where R is aryl or alkyl and n=1-6, can be used to reduce the aggregation tendency and have positive effects on the photophysical properties of dyes.

Where a substituent is further substituted by a functional group $R^\pm$ that is ionically charged, such as for example a carboxylic acid, sulfonic acid, phosphoric acid, phosphonate or a quaternary ammonium group, the ionic substituent $R^\pm$ may serve to increase the overall hydrophilicity of the compound.

As used herein, functional groups such as "carboxylic acid," "sulfonic acid," and "phosphoric acid" include the free acid moiety as well as the corresponding metal salts of the acid moiety, and any of a variety of esters or amides of the acid moiety, including without limitation alkyl esters, aryl esters, and esters that are cleavable by intracellular esterase enzymes, such as alpha-acyloxyalkyl ester (for example acetoxymethyl esters, among others).

The compounds of the invention are optionally further substituted by a reactive functional group $R^x$, or a conjugated substance $S_c$, as described below.

The compounds of the invention may be depicted in structural descriptions as possessing an overall charge, it is to be understood that the compounds depicted include an appropriate counter ion or counter ions to balance the formal charge present on the compound. Further, the exchange of counter ions is well known in the art and readily accomplished by a variety of methods, including ion-exchange chromatography and selective precipitation, among others.

Carriers and Conjugated Substances $S_c$

The reporter compounds of the invention, including synthetic precursor compounds, may be covalently or non-covalently associated with one or more substances. Covalent association may occur through various mechanisms, including a reactive functional group as described above, and may involve a covalent linkage, -L-, separating the compound or precursor from the associated substance (which may therefore be referred to as $-L-S_c$).

A covalent linkage binds the reactive group $R^x$, the conjugated substance $S_c$ or the ionic group $R^\pm$ to the dye molecule, either directly via a single covalent bond which is depicted in the text as $—R^x$, $—R^\pm$, $—S_c$, or with a combination of stable chemical bonds (-L-), that include single, double, triple or aromatic carbon-carbon bonds; carbon-sulfur bonds, carbon-nitrogen bonds, phosphorus-sulfur bonds, nitrogen-nitrogen bonds, nitrogen-oxygen or nitrogen-platinum bonds, or aromatic or heteroaromatic bonds; -L- includes ether, thioether, carboxamide, sulfonamide, urea, urethane or hydrazine moieties. Preferably, -L- includes a combination of single carbon-carbon bonds and carboxamide or thioether bonds.

Where the substance is associated non-covalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Waals forces). The associated carrier may be selected from the group consisting of polypeptides, polynucleotides, polysaccharides, beads, microplate well surfaces, metal surfaces, semiconductor and non-conducting surfaces, nanoparticles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland et al., MOLECULAR PROBES HANDBOOK OF FLUORES- CENT PROBES AND RESEARCH CHEMICALS, Eighth Edition (1996), or G. T. Hermanson, Bioconjugate Techniques, Academic Press, London, (1996), which is hereby incorporated by reference. Typically, the association or conjugation of a chromophore or luminophore to a substance imparts the spectral properties of the chromophore or luminophore to that substance.

Useful substances for preparing conjugates according to the present invention include, but are not limited to, amino acids, peptides, proteins, phycobiliproteins, nucleosides, nucleotides, nucleic acids, carbohydrates, lipids, ion-chelators, biotin, pharmaceutical compounds, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be an enzyme, an antibody, lectin, protein A, protein G, hormones, or a phycobiliprotein. The conjugated substance may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA.

Another class of carriers includes carbohydrates that are polysaccharides, such as dextran, heparin, glycogen, starch and cellulose.

Where the substance is an ion chelator, the resulting conjugate may be useful as an ion indicator (calcium, sodium, magnesium, zinc, potassium and other important metal ions) particularly where the optical properties of the reporter-conjugate are altered by binding a target ion. Preferred ion-complexing moieties are crown ethers (U.S. Pat. No. 5,405,957) and BAPTA chelators (U.S. Pat. No. 5,453,517).

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen—antibody, biotin—avidin, biotin—streptavidin, IgG—protein A, IgG—protein G, carbohydrate—lectin, enzyme—enzyme substrate; ion—ion-chelator, hormone—hormone receptor, protein—protein receptor, drug—drug receptor, DNA—antisense DNA, and RNA—antisense RNA.

Preferably, the associated or conjugated substance includes proteins, carbohydrates, nucleic acids, drugs, and nonbiological polymers such as plastics, metallic nanoparticles such as gold, silver and carbon nanostructures among others. Further carrier systems include cellular systems (animal cells, plant cells, bacteria). Reactive dyes can be used to label groups at the cell surface, in cell membranes, organelles, or the cytoplasm.

Finally these compounds can be linked to small molecules such as amino acids, vitamins, drugs, haptens, toxins, and environmental pollutants, among others. Another important ligand is tyramine, where the conjugate is useful as a substrate for horseradish peroxidase.

Synthesis and Characterization

The synthesis of the disclosed reporter compounds typically is achieved in a multi-step reaction. The syntheses of representative dyes and reactive labels are provided in the Examples section below. While the syntheses of non-reactive dyes have been previously described, reactive version and conjugates of these compounds have not been described earlier. The fluorescent properties of representative dyes are given in Table 1.

EXAMPLES

This section describes the synthesis of representative dyes of this invention. The spectral properties as well as the luminescent lifetimes of representative dyes in various solvents are summarized in Table 1 below. The fluorescence lifetime properties of these compounds have not been disclosed earlier.

Example 1

Synthesis of Precursors

The phenylimide (1) and 4-carboxyphenylimide of 4-dimethyl aminonaphthalic acid (2a) were synthesized according to the method described in (USSR Patent 1262911), respectively.

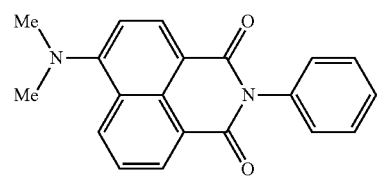

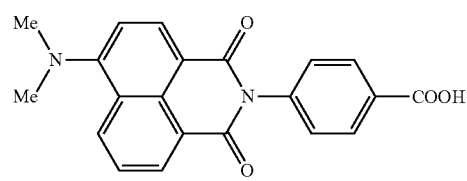

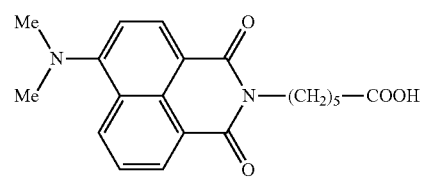

1: Yield 59%. M.P. 269-271° C.
2a: Yield 70%. M.P. 315-318° C.
2b: Yield 20%. M.P. 125-128° C.

Synthesis of 6-(5-dimethylamino-1,3-dioxo-2,3-dihydro-1H-benzo[de]-isoquinolin-2-yl)hexanoic acid (Dye 2c)

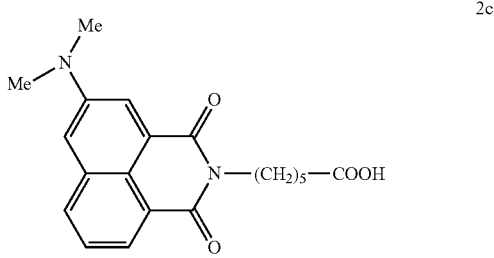

2.45 g (0.01 mmol) of 5-nitro-1H,3H-benzo[de]isochromene-1,3-dione and 1.23 g (0.01 mmol) of 6-aminohexanoic acid was alloyed with at 210-220° C. for 35 min. The obtained crude 6-(5-nitro-1,3-dioxo-2,3-dihydro-1H-benzo[de]isoquinolin-2-yl)hexanoic acid was recrystallized from ethanol. Yield 1.7 g (48%). The product was dissolved in 50 mL of ethanol and was added dropwise to the hot solution of 8 g of tin chloride in 9 mL of hydrochloric acid at boiling. The reaction mixture was boiled for 4 h, then poured with water and neutralized with 5% solution of sodium hydrate. Yellow sediment was filtered and purified by a column chromatography (Silica gel, chloroform). Yield 1.1 g of ethyl 6-(5-amino-1,3-dioxo-2,3-dihydro-1H-benzo[de]isoquinolin-2-yl)hexanoate (31.5% counting on 5-nitro-1H,3H-benzo[de]isochromene-1,3-dione). M.P. 108-110° C.

A mixture of 1.8 g (5.08 mmol) of ethyl 6-(5-amino-1,3-dioxo-2,3-dihydro-1H-benzo[de]isoquinolin-2-yl)hexanoate in 9 mL of chloroform was added at 40° C. to a solution of 1.35 g (13.2 mmol) of sodium hydrocarbonate in 6 mL of water. Then 1.3 mL (17.6 mmol) of dimethyl sulfate was added and heated under stirring at 40° C. for 1 h.
The reaction mixture was heated at 55-60° C. for 20 min, cooled to RT and dilute with chloroform. The solvent was removed and the residue was suspended in 20 mL of acetic anhydride and heated on the water bath for 40 min. The reaction mixture was poured into water, neutralized with ammonia and extracted with chloroform. The product was column purified (Silica gel, chloroform). The obtained 0.6 g (30%) of ethyl 6-(5-dimethylamino-1,3-dioxo-2,3-dihydro-1H-benzo[de]isoquinolin-2-yl)hexanoate was treated with 0.1 M solution of HCl to yield 0.42 g (75%) of 6-(5-dimethylamino-1,3-dioxo-2,3-dihydro-1H-benzo[de]isoquinolin-2-yl)hexanoic acid. M.p. 111-114° C. $^1$H-NMR (200 MHz, DMSO-$d_6$, δ, ppm): 8.21-7.42 (5H, arom), 3.99 t (2H, α-CH$_2$, J 7.3 Hz), 3.11 s (6H, N(CH$_3$)$_2$), 2.21 t (2H, ε-CH$_2$, J 7.3 Hz), 1.56 m (4H, β,γ-CH$_2$ J 7.3 Hz), 1.36 m (2H, δ-CH$_2$, J 7.3 Hz).

Example 2

Dyes 3, 4 and 5 were synthesized according to procedures described in (L. D. Patsenker et al., Tetrahedron, 2000, V.56, No. 37, P. 7319-7323).

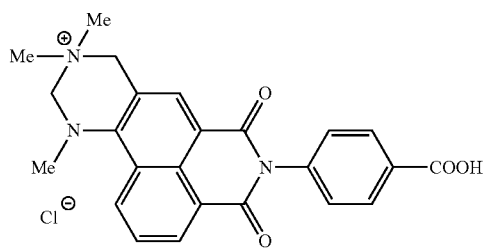 [SMILES: CN1C[N+](C)(C)Cc2cc3c4c(cccc4c21)C(=O)N(c1ccc(C(=O)O)cc1)C3=O ; [Cl-]]

3

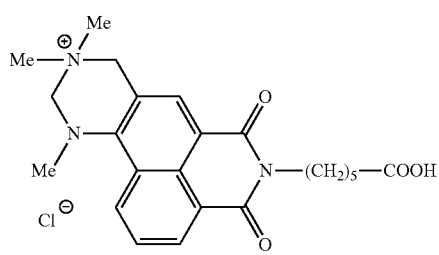

4

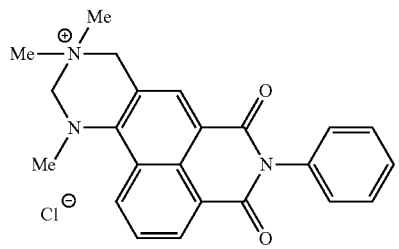 [SMILES: CN1C[N+](C)(C)Cc2cc3c4c(cccc4c21)C(=O)N(c1ccccc1)C3=O ; [Cl-]]

5

Synthesis of 5-(4-carboxyphenyl)-9,9,11-trimethyl-4, 6-dioxo-5,6,8,9,10,11-hexahydro-4H-isoquino[4,5-g, h]quinazolin-9-ium chloride (3)

1.26 g (4 mmol) of 4-carboxyphenylimide of 4-dimethylaminonaphthalic acid (2) were dissolved in 5 mL (65 mmol) of DMF, and then 1.7 mL (18 mmol) of POCl$_3$ were added dropwise at 60-70° C. The mixture was heated with stirring at 100° C. for 25 min, cooled to RT and poured into ice water. Yield 0.92 g (51%), yellow solid. M.P. 255-258° C. Found: C, 63.9; H, 4.8; Cl, 7.8; N, 9.4. C$_{24}$H$_{21}$ClN$_3$O$_4$. Calculated: C, 63.93; H, 4.69; Cl, 7.86; N, 9.32%; IR, $ν_{max}$(KBr) 1715, 1695, 1660, 1600, 1570, 1465, 1404, 1380, 1350, 1280, 1240 cm$^{-1}$; $^1$H-NMR (300 MHz, DMSO-$d_6$, δ, ppm) 3.32 (6 H, s, $^+$N(CH$_3$)$_2$), 3.73 (3 H, s, 4-NCH$_3$), 5.01 (2 H, s, CH$_2$), 5.25 (2 H, s, CH$_2$), 7.38-8.67 (8 H, m, arom H).

Synthesis of 5-(5-carboxypentyl)-9,9,11-trimethyl-4, 6-dioxo-5,6,8,9,10,11-hexahydro-4H-isoquino[4,5-gh]quinazolin-9-ium chloride (4)

To a mixture of 0.177 g (0.5 mmol) of 2b and 0.5 mL (6.5 mmol) of DMF 0.18 mL (2 mmol) of POCl$_3$. The mixture was heated at 80° C. for 1.5 h, treated with ice, and aceton was added to precipitate the oiled product, which was treated with ether to give 4 as yellow crystals.

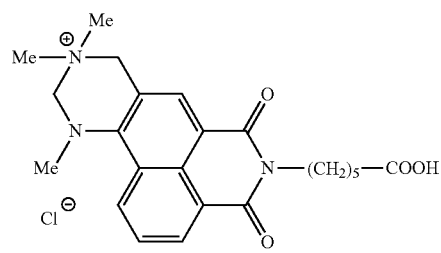

4

Synthesis of 5-(5-carboxypentyl)-8,10,10-trimethyl-4,6-dioxo-5,6,8,9,10,11-hexahydro-4H-isoquino[5,4-fg]quinazolin-10-ium chloride (4a)

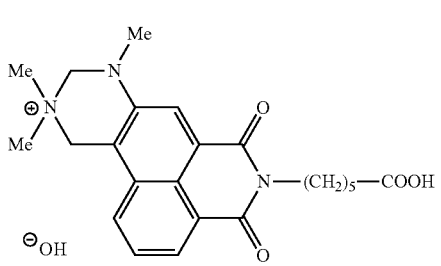

4a

To a solution of 90 mg (0.25 mmol) of 6-(5-dimethylamino-1,3-dioxo-2,3-dihydro-1H-benzo[de]isoquinolin-2-yl)hexanoic acid in 0.4 mL of DMF 0.09 ml of POCl₃ were added dropwise at 40° C. The mixture was heated under stirring at 80° C. for 1.5 h, cooled to RT and poured into ice water. The product was precipitated with isopropyl alcohol and purified by column chromatography on reverse phase (PR-18, H₂O-acetonitrile 5:1, v/v). Yield: 45 mg (40%) 4a. M.p. 186-188° C. ¹H-NMR (200 MHz, DMSO-d₆, δ, ppm): 8.39-7.82 (5H, arom), 5.17 s (2H, CH₂), 4.85 s (2H, CH₂), 4.04 t (2H, α-CH₂, J 7.3 Hz), 3.65 s (3H, NCH₃), 3.19 s (6H, ⁺N(CH₃)₂), 1.94 t (2H, ε-CH₂, J 7.3 Hz), 1.54 m (4H, β,γ-CH₂ J 7.3 Hz), 1.26 m (2H, δ-CH₂, J 7.3 Hz).

Synthesis of 9,9,11-trimethyl-4,6-dioxo-5-phenyl-5,6,8,9,10,11-hexahydro-4H-isoquino[4,5-g,h]quinazolin-9-ium chloride (5)

Compound 5 was obtained by the same procedure as 3 using 1.44 g (4 mmol) of phenylimide instead of carboxyphenylimide. The crude product was recrystallized from ethanol to give the 5 (0.86 g, 53%) as a yellow solid, M.P. 235° C. Found: C, 66.3; H, 5.5; Cl, 8.7; N, 10.4. C₂₃H₂₂ClN₃O₂·0.5H₂O. Calculated: C, 66.26; H, 5.56; Cl, 8.50; N, 10.08%. IR, ν_max(KBr) 1695, 1650, 1600, 1565, 1450, 1400, 1375, 1340 cm⁻¹. ¹H-NMR (300 MHz, DMSO-d₆, δ, ppm) 3.42 (6 H, s, ⁺N(CH₃)₂), 3.88 (3 H, s, 4-NCH₃), 5.00 (2 H, s, CH₂), 5.16 (2 H, s, CH₂), 7.42-8.86 (9 H, m, arom H).

Example 3

Synthesis of 8,10,10-trimethyl-4,6-dioxo-5-phenyl-5,6,8,9,10,11-hexahydro-4H-isoquino[5,4-fg]quinazolin-10-ium hexafluorophosphate (6)

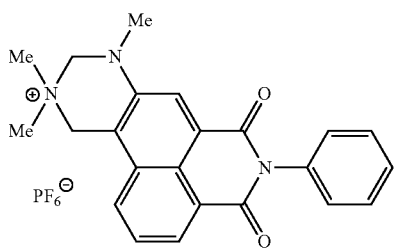

To a mixture of 3.16 g (0.01 mol) of phenylimide 3-dimethylaminonaphthalic acid and 13.8 mL (0.18 mol) of DMF at 30-35° C. 4.1 mL (0.045 mol) of POCl₃ were added dropwise. The mixture was stirred at 80° C. for 30 min, cooled down to RT, and treated with ice. Then LiPF₆ was added and the obtained precipitate was filtered off and dried. Yield 3.10 g (60%). M.P. 259-260° C. ¹H-NMR (300 MHz, δ, ppm,): 8.36 d (1H, H⁷, J 7.3 Hz), 8.18 s (1H, H⁵), 8.14 d (1H, H², J 8.4 Hz), 7.93 dd (1H, H⁶, J₁ 8.3, J₂ 7.4 Hz), 7.59-7.34 m (5H, phenyl), 5.22 s (2H, CH₂), 4.87 s (2 H, CH₂), 3.39 s (3H, N—CH₃), 3.22 s (6H, ⁺N(CH₃)₂). Found, %: C, 53.35; H, 4.30; N, 10.99. C₂₃H₂₂F₆N₃O₂P. Calculated, %: C, 53.39; H, 4.26; N, 11.25.

Example 4

Dyes 7a, 7b, and 8 were synthesized according to (O. N. Lyubenko, et al., Chem. Heterocycl. Compd., Engl. Transl., 2003, No. 4, P. 594).

Synthesis of Intermediate isomeric ethyl 4-dimethylamino- (Ia) and ethyl 3-dimethylamino (Ib) -10-methyl-7-oxo-7H-benzo[de]pyrazolo[5,1-a]isoquinoline-11-carboxylates

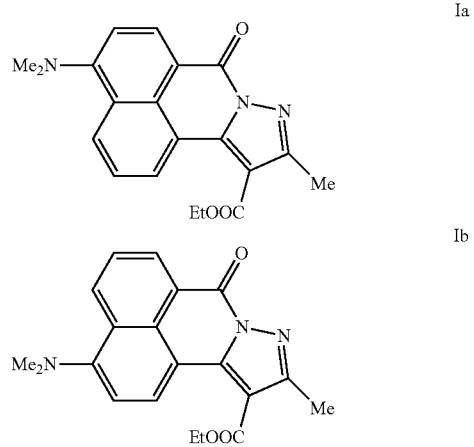

A mixture of 5 mmol of 2-amino-6-dimethylamino-2,3-dihydro-1H-benzo[de]isoquinoline-1,3-dione (O. N. Lyubenko, et al., Chem. Heterocycl. Compd., Engl. Transl., 2003, No. 4, P. 594), 4.5 mL (35 mmol) of acetoacetic acid diethyl ester and 0.01 g (0.057 mmol) p-toluenesulfonic acid was stirred at 130° C. for 4 h under nitrogen atmosphere. The obtained precipitate of hydrazone was filtered off, washed with methanol, water, and dried. Then the hydrazone was refluxed for 1 h in 2.5 mL of DMF and 0.01 g (0.12 mmol) of NaOAc. The precipitate was filtered off, washed with methanol, water, and dried. Isomeric dyes Ia and Ib were separated using a column chromatography (Al₂O₃, benzene). Ia. Yield 18%. M.P. 204-205° C. ¹H-NMR, (200 MHz, DMSO-d₆, δ, ppm): 9.28 (1H, d, J=7.6, 7-H), 8.52 (1H, d, J=8.5, 2-H), 8.38 (1H, d, J=8.5, 5-H), 7.68 (1H, t, J=8.0, 6-H), 7.24 (1H, d, J=8.5, 3-H), 7.2; COOCH₂CH₃), 4.42 (2H, q, J=14.1), 3.19 (6H, s, N(CH₃)₂), 2.50 (3H, s, CH₃), 1.39 (3H, t, J=7.2, COOCH₂CH₃). Found, %: C, 68.70; H, 5.38; N, 11.60. C₂₀H₁₉N₃O₃. Calculated, %: C, 68.77; H, 5.44; N, 12.03. IR (ν, cm⁻¹, KBr): 1680 (C=O carbonyl), 1710 (C=O ester). Ib. Yield 12%. M.P. 194-195° C. ¹H-NMR, (200 MHz, DMSO-d₆, δ, ppm): 9.26 (1H, d, J=8.4, 7-H), 8.68 (1H, d, J=7.3, 2-H), 8.62 (1H, dd., J=8.4; 0.7; 4-H), 7.83 (1H, t, J=7.9, 3-H), 7.18 (1H, d, J=8.5, 6-H), 4.38 (2H, q, J=14.2; 7.1; COOCH₂CH₃), 3.07 (6H, s, N(CH₃)₂), 2.48 (3H, s, CH₃), 1.39 (3H, t, J=7.1, COOCH₂CH₃). Found, %: C, 68.71; H, 5.40; N, 11.79. C₂₀H₁₉N₃O₃. Calculated, %: C, 68.77; H, 5.44; N, 12.03. IR (ν, cm⁻¹, KBr): 1680 (C=O carbonyl), 1710 (C=O ester).

General procedure for the synthesis of dyes 7a, 7b, an

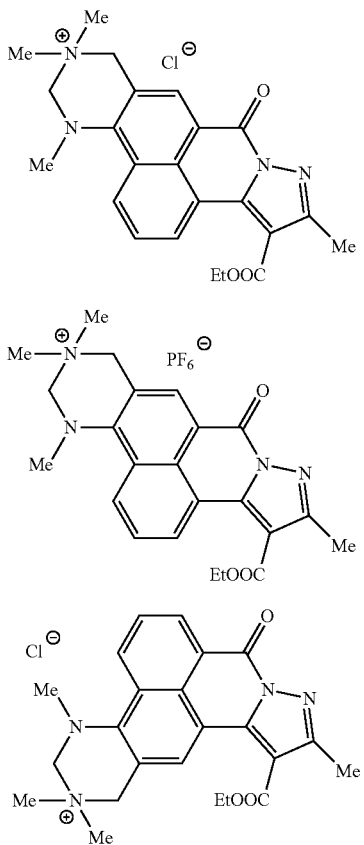

To a mixture of 1 mmol of pyrazole Ia or Ib in 2 mL (26 mmol) of DMF at 60° C. 0.37 mL (4 mmol) of POCl$_3$ was added dropwise. The mixture was stirred at 100° C. for 3 h in case of Ia and 4 h in case of Ib, cooled down and poured into ice. 13-Acetyl-4,6,6,12-tetramethyl-9-oxo-4,6,7,9-tetrahydro-5H-pyrazolo[5',1':1,2]isoquino[4,5-gh]quinazoline-6-ium chloride (7a) and 12-acetyl-2,2,4,11-tetramethyl-8-oxo-2,3,4,8-tetrahydro-1H-pyrazolo[1',5':2,3]isoquino[4,5-gh]quinazoline-2-ium chloride (8) were precipitated by isopropanol. Chlorides 7a and 13 were recrystallized from ethanol. Crystalline 13-acetyl-4,6,6,12-tetramethyl-9-oxo-4,6,7,9-tetrahydro-5H-pyrazolo-[5',1':1,2]isoquino[4,5-gh]quinazoline-6-ium hexafluorophosphate 7b was obtained using 0.15 g (1 mmol) of LiPF$_6$, and then was column purified (Silochrom C-120, acetonitrile). 7a: Yield 30%. M.P. 251-252° C. (ethanol). $^1$H-NMR (200 MHz, DMSO-d$_6$, δ, ppm): 9.27 (1H, d, J=7.6, 7-H), 8.39 (1H, d J=8.6, 5-H), 8.32 (1H, s 2-H), 7.75 (1H, t J=8.2, 6-H), 5.17 (2H, s CH$_2$), 5.02 (2H, s CH$_2$), 4.42 (2H, q, J=14.0; 7.0; COOCH$_2$CH$_3$), 3.72 (3H, s, NCH$_3$), 3.31 (6H, s, N$^+$(CH$_3$)$_2$), 2.49 (3H, s, CH$_3$), 1.41 (3H, t, J=7.2, COOCH$_2$CH$_3$). Found, %: C, 62.59; H, 5.73; N, 12.23; Cl 7.89. C$_{23}$H$_{25}$N$_4$O$_3$Cl. Calculated, %: C, 62.65; H, 5.67; N, 12.71; Cl 8.06. IR (v, cm$^{-1}$, KBr): 1680 (C=O carbonyl), 1700 (C=O ester). 7b: Yield 45%. M.P. 315-318° C. (acetonitrile). $^1$H-NMR (200 MHz, DMSO-d$_6$, δ, ppm): 1.41 (3H, t, J=7.1, COOCH$_2$CH$_3$); 2.52 (3H, s, CH$_3$); 3.24 (6H, s, N$^+$(CH$_3$)$_2$); 3.69 (3H, s, NCH$_3$); 4.44 (2H, q, J=14.1; 7.0; COOCH$_2$CH$_3$); 4.93 (2H, s, CH$_2$); 5.06 (2H, s, CH$_2$); 7.84 (1H, t, J=8.1, 6-H); 8.45 (1H, s, 2-H); 8.46 (1H, d, J=7.9, 5-H); 9.36 (1H, d, J=7.6, 7-H). Found, %: C, 50.11; H, 4.46; N, 10.54. C$_{23}$H$_{25}$N$_4$O$_3$PF$_6$. Calculated, %: C, 50.18; H, 4.54; N, 10.18. IR (v, cm$^{-1}$, KBr): 1700 (C=O carbonyl), 1680 (C=O ester). 8: Yield 34%. M.P. 242-245° C. (ethanol). $^1$H-NMR (200 MHz, DMSO-d$_6$, δ, ppm): 1.41 (3H, t, J=7.2, COOCH$_2$CH$_3$); 2.54 (3H, s, CH$_3$); 3.30 (6H, s, N$^+$(CH$_3$)$_2$); 3.68 (3H, s, NCH$_3$); 4.41 (2H, q, J=14.1; 7.2; COOCH$_2$CH$_3$); 4.92 (2H, s, CH$_2$); 5.11 (2H, s, CH$_2$); 7.91 (1H, t, J=7.9, 3-H); 8.65 (1H, d, J=6.3, 2-H); 8.68 (1H, d, J=8.2, 4-H); 9.16 (1H, s, 7-H). Found, %: C, 62.59; H, 5.72; N, 12.66; Cl 8.23. C$_{23}$H$_{25}$N$_4$O$_3$Cl. Calculated, %: C, 62.65; H, 5.67; N, 12.71; Cl 8.06. IR (v, cm$^{-1}$, KBr): 1650 (C=O carbonyl), 1700 (C=O ester).

Analogously to the reaction described above the carboxylated version of these dyes can be synthesized using the free acids of Ia and Ib instead of the ethyl esters as starting materials.

Example 5

Synthesis of 1,3,3-Trimethyl-6-(5-phenyl-1,3,4-oxadiazol-2-yl)-1,2,3,4-tetrahydroquinazolin-3-ium chloride (9)

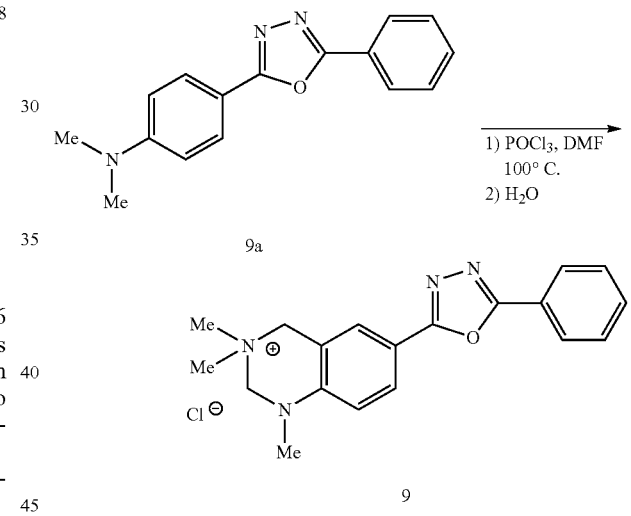

POCl3 (0.6 ml, 6.6 mmol) was added dropwise to a suspension of the oxadiazole 9a (0.55 g, 2.0 mmol) in DMF (2.5 ml, 32.5 mmol) at 60-70° C. The reaction product was stirred for 5 h at 100° C., cooled to room temperature, and poured onto a small amount of ice. Addition of acetone precipitated an oily material which crystallized after 12 h. Recrystallization from DMF gave a colorless crystalline material 9. Yield 0.22 g (30%); M.P. 272-273° C. (DMF). IR spectrum, v, cm−1: 1610, 1585, 1450, 1430, 1390, 1300, 1210. 1H NMR spectrum, δ, ppm (J, Hz): 3.15 (6H, s, +N(CH3)2); 3.20 (3H, s, NCH3); 4.79 (2H, s, CH2); 4.86 (2H, s, CH2); 7.15 (1H, d, J=8.8, 2-H); 7.60-7.68 (3H, s, Ph); 7.91 (1H, s, 1-H); 8.04 (1H, dd, J1=8.5, J2=1.9, 3-H); 8.08-8.17 (2H, m, Ph). Found, %: C, 63.81; H, 9.72; Cl 9.56; N 15.50. C19H21ClN4O. Calculated, %: C, 63.95; H, 5.89; Cl 9.96; N 15.71.

Analogously the carboxylated version of 1,3,3-trimethyl-6-(5-phenyl-1,3,4-oxadiazol-2-yl)-1,2,3,4-tetrahydroquinazolin-3-ium chloride is synthesized using 2-(4-carboxyphenyl)-5-(4-dimethylaminophenyl)-1,3,4-oxadiazole as the starting material.

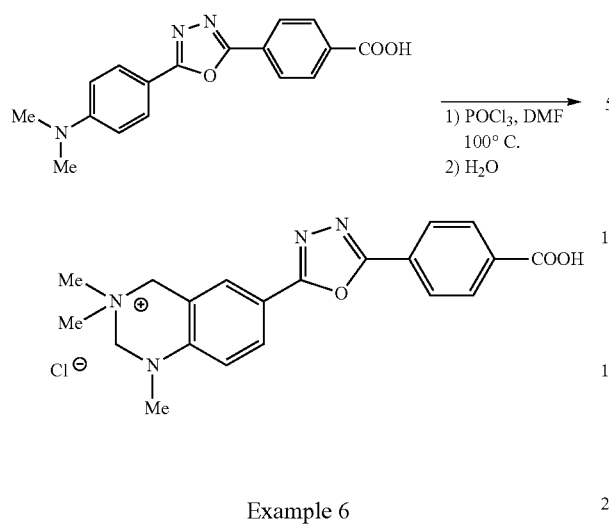

Example 6

Synthesis of 1,3,3-Trimethyl-6-(5-phenyl-1,3-oxazol-2-yl)-1,2,3,4-tetrahydroquinazolin-3-ium hexafluorophosphate (10)

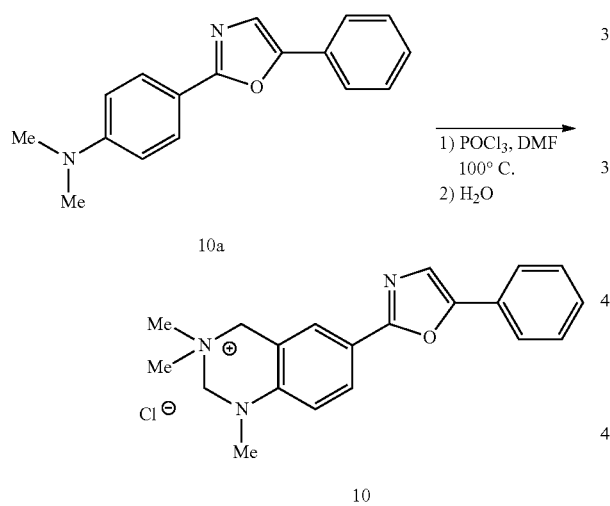

POCl3 (1.1 ml, 12.0 mmol) was added dropwise to a mixture of the oxazole 10a (0.52 g, 2.0 mmol) in DMF (2.5 ml, 32.5 mmol) at 60-70° C. The reaction mixture was held for 7 h at 100° C., cooled, and poured onto ice. NH4 PF6 (0.32 g, 2.0 mmol) was added and a finely crystalline precipitate was formed. Purification by column chromatography on silica gel (eluent acetonitrile) gave colorless crystals. Yield: 0.2 g (23%) 10; M.P. 220-222° C. IR spectrum, v, cm−1: 1620, 1500, 830 (PF6). 1H NMR spectrum, δ, ppm (J, Hz): 3.12 (6H, s, +N(CH3)2); 3.18 (3H, s, NCH3); 4.73 (2H, s, CH2); 4.76 (2H, s, CH2); 7.09 (1H, d, J=8.7, 2-H); 7.73 (1H, s, 4-H); 7.82 (1H, s, 1-H); 7.99 (1H, dd, J1=8.6, J2=1.9, 3-H); 7.86-7.30 (5H, m, Ph). Found, %: C, 51.47; H, 4.62; N 9.23. C20H22F6N3OP. Calculated, %: C, 51.61; H, 4.73; N, 9.03.

Analogously the carboxylated version of 1,3,3-Trimethyl-6-(5-phenyl-1,3-oxazol-2-yl)-1,2,3,4-tetrahydroquinazolin-3-ium hexafluorophosphate (10) is synthesized by using 2-(4-carboxyphenyl)-5-(4-dimethylaminophenyl)-1,3-oxazole as the starting material.

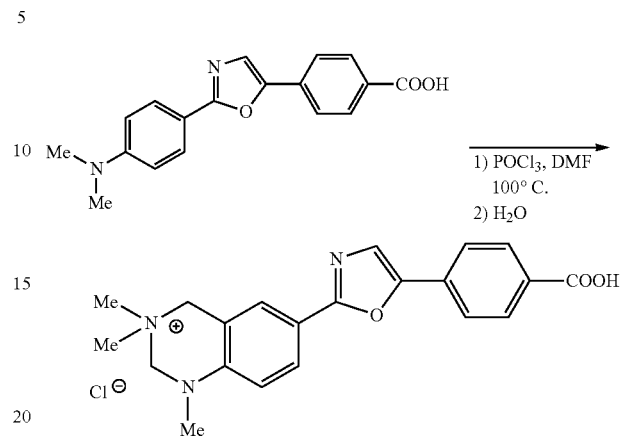

Example 7

Synthesis of 1,3,3-Trimethyl-6-[5-(1,3,3-trimethyl-1,2,3,4-tetrahydro quinazolin-3-ium]-6-yl)-1,3,4-oxadiazol-2-yl]-1,2,3,4-tetrahydroquinazolin-3-ium Dichloride (11)

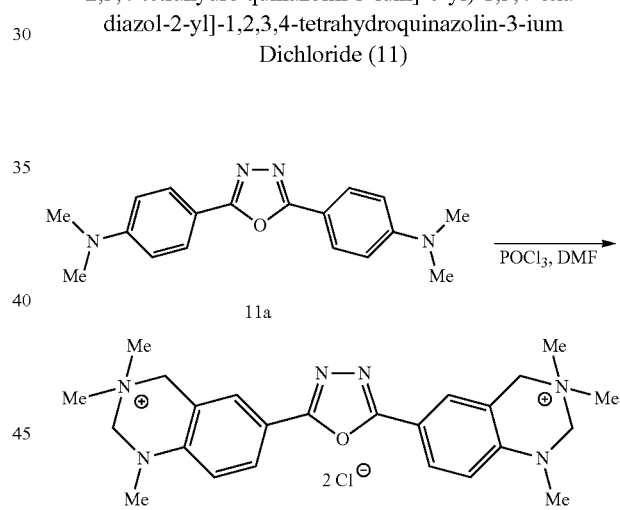

POCl3 (1.4 ml, 15.3 mmol) was added dropwise to a suspension of the oxadiazole 11a (0.93 g, 3.0 mmol) in DMF (4 ml, 52.0 mmol) at 60-70° C. The reaction mixture was stirred for 3 h at 100° C., cooled to room temperature, and diluted with a small amount of 96% ethanol to give colorless crystals. Yield: 0.9 g (60%) 11; mp 318-320° C. (ethanol). IR spectrum, v, cm−1: 1610, 1500, 1450, 1410, 1330, 1240. 1H NMR spectrum, δ, ppm (J, Hz): 3.16 (12H, s, 2+N(CH3)2); 3.20 (6H, s, 2 NCH3); 4.78 (4H, s, 2 CH2); 4.84 (4H, s, 2 CH2); 7.15 (2H, d, J=8.8, 2-H); 7.86 (2H, s, 1-H); 8.01 (2H, dd, J1=8.7, J2=1.2, 3-H). Mass spectrum, m/z 390 [M-2CH3Cl]+. Found, %: C, 58.46; H, 6.37; Cl 14.41; N 17.12. C24H32Cl2N6O. Calculated, %: C, 58.66; H, 6.52; Cl 14.46; N 17.11.

Example 8

Synthesis of 1,3,3-trimethyl-8-oxo-2,3,4,8-tetrahydro-1H-anthra[1,9-fg]-quinazolin-3-ium hexafluorophosphate (12)

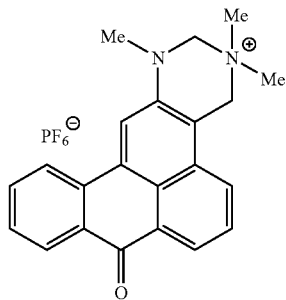

2.73 g (0.1 mol) of 2-dimethylamino benzanthrone was dissolved in 4.6 mL (0.06 mol) of DMF and 3.66 mL (0.04 mol) of $POCl_3$ were added dropwise at 35-40° C. The mixture was heated with stirring at 80° C. for 1.5 h, cooled down to RT and treated with ice. Then $NH_4PF_6$ was added and the obtained precipitate was recrystallized from a water-ethanol (1:1, v/v) mixture. Yield 3.18 g (67%) 12. M.P. 295-297° C. $^1$H-NMR, (200 MHz, DMSO-$d_6$, δ, ppm): 8.79 d (1H, $H^6$, J 8.2 Hz), 8.47 d (1H, $H^7$, J 7.6 Hz), 8.45 s (1H, $H^1$), 8.33 d (1H, $H^{10}$, J 7.5 Hz), 8.11 d (1H, $H^4$, J 8.3 Hz), 7.90 t (2H, $H^8$, $H^9$, J 7.6 Hz), 7.68 t (1H, $H^5$, J 8.0 Hz), 5.15 s (2H, $CH_2$), 4.86 s (2H, $CH_2$), 3.51 s (3H, $NCH_3$), 3.22 s (6H, $^+N(CH_3)_2$). Found, %: C, 55.58; H, 4.62; N, 5.39. $C_{22}H_{21}N_2OPF_6$. Calculated, %: C, 55.70; H, 4.46; N, 5.91.

Example 9

Synthesis of 2,2,4-trimethyl-1,2,3,4-tetrahydronaphtho[2,3-f]quinazolin-2-ium hexafluorophosphate (16)

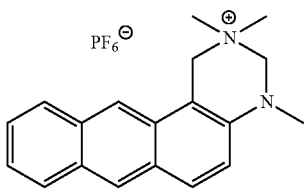

2.21 g (10 mmol) of 2-dimethylaminoanthracene was added at 0-5° C. to a mixture of 4.2 mL (55 mmol) DMF and 1.83 mL (20 mmol) of $POCl_3$. The mixture was heated with stirring at 80° C. for 3 h, cooled down to RT, treated with ice, neutralized with AcONa, and $NH_4PF_6$ was added. The obtained precipitate was recrystallized from aqueous ethanol. Yield 2.74 g (65%) 13. M.P. 255-256° C. $^1$H-NMR, (200 MHz, DMSO-$d_6$, δ, ppm): 8.57 s (1H, $H^9$), 8.14 s (1H, $H^{10}$), 8.11 d (1H, $H^4$, J 9.4 Hz), 8.06 d (2H, $H^5$, $H^8$, J 8.3 Hz), 7.60 m (2H, $H^6$, $H^7$, J 8.3 Hz), 7.49 d (1H, $H^3$, J 9.3 Hz), 5.08 s (2H, $CH_2$), 4.83 s (2H, $CH_2$), 3.25 s (3H, $NCH_3$), 3.22 s (6H, $^+N(CH_3)_2$). Found, %: C, 54.22; H, 5.17; N, 6.81. $C_{19}H_{21}N_2PF_6$. Calculated, %: C, 54.03; H, 5.01; N, 6.63.

Example 11

General Procedure for Labelling of Proteins and Determination of Dye-to-Protein Ratios Protein labelling reactions were carried out using a 50 mM bicarbonate buffer (pH 9.1). A stock solution of 1 mg of dye in 100 µL of anhydrous DMF was prepared. 10 mg of protein were dissolved in 1 mL of 100 mM bicarbonate buffer (pH 9.1). Dye from the stock solution was added, and the mixture was stirred for 24 h at room temperature.

Unconjugated dye was separated from labelled proteins using gel permeation chromatography with SEPHADEX G50 (0.5 cm×20 cm column) and a 22 mM phosphate buffer solution (pH 7.3) as the eluent. The first colored or/and fluorescent band contained the dye-protein conjugate. A later colored or/and fluorescent band with a much higher retention time contained the separated free dye. A series of labelling reactions as described above were set up to obtain different dye-to-protein ratios. Compared to the free forms, the protein-bound forms of the dyes show distinct changes in their spectral properties.

The dye-to-protein ratio (D/P) gives the number of dye molecules covalently bound to the protein. The D/P ratio was determined according to [R. B. Mujumdar, L. A. Ernst, S. R. Mujumdar, C. J. Lewis, A. S. Waggoner, Bioconjugate Chem., 4 (1993) 105-111]. Each dye—BSA conjugate was diluted with phosphate buffer (PB) pH 7.4 to provide the absorbance ($A_{conj(\lambda max)}$) in a 5-cm quartz cuvette in the range of 0.15-0.20 at the long-wavelength absorption maximum of the dye—BSA conjugate. For these solutions the absorbances $A_{conj\,(\lambda max)}$ at the long-wavelength maximum of the dye and $A_{conj(278)}$ at 278 nm were measured. Then the absorbances of the free dye at 278 nm ($A_{dye(278)}$) and at the long-wavelength maximum ($A_{dye(\lambda max)}$) were taken from the dye absorption spectrum. The dye-to-protein ratio (D/P) were calculated using the following formula:

$$D/P = \frac{A_{conj(\lambda max)} \varepsilon_{BSA}}{(A_{conj(278)} - xA_{conj(\lambda max)})\varepsilon_{dye}},$$

where $\varepsilon_{dye}$ is the extinction coefficient of the dye at the long-wavelength maximum, and $\varepsilon_{BSA}$=45540 $M^{-1}cm^{-1}$ is the extinction coefficient of BSA at 278 nm, and $x=A_{dye(278)}/A_{dye(\lambda max)}$.

Covalent Attachment of NHS-Esters to BSA

A stock solution of 1 mg of NHS-ester in 100 µL of anhydrous DMF was prepared. Then 5 mg of BSA was dissolved in 1 mL of a 50 mM bicarbonate buffer, pH 9.0, and a relevant amount of the dye stock solution was added. The mixture was allowed to stir for 3 h at 25° C. Separation of the dye-BSA conjugate from non-conjugated dye was achieved using gel permeation chromatography on a 1.5 cm×25 cm column (stationary phase: Sephadex G25; eluent: 67 mM PB, pH 7.4). The fraction with the lowest retention time containing the dye-BSA conjugate was collected.

Covalent Attachment of NHS-Esters to Polyclonal Anti-HSA (IgG)

385 µL (5.2 mg/mL) of anti-HSA were dissolved in a 750 µL bicarbonate buffer (0.1 M, pH 9.0). 1 mg of NHS-ester is dissolved in 50 μL of DMF and slowly added to the above-prepared protein solution with stirring. After 20 h of stirring, the protein-conjugate was separated from the free dye using Sephadex G50 and a phosphate buffer (22 mM, pH 7.2). The first colored or/and fluorescent fraction that is isolated contains the labeled conjugate.

Example 12

Synthesis of 5-[4-(2,5-dioxotetrahydro-1H-1-pyrrolyloxycarbonyl)phenyl]-9,9,11-trimethyl-4,6-dioxo-5,6,8,9,10,11-hexahydro-4H-isoquino[4,5-gh]quinazolin-9-ium chloride (3-NHS)

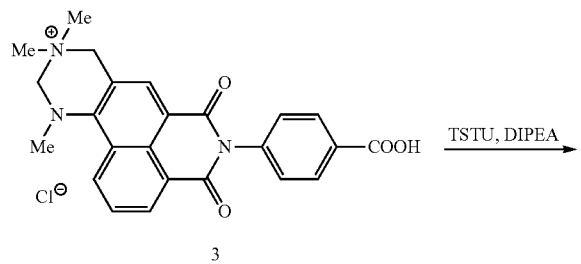

3

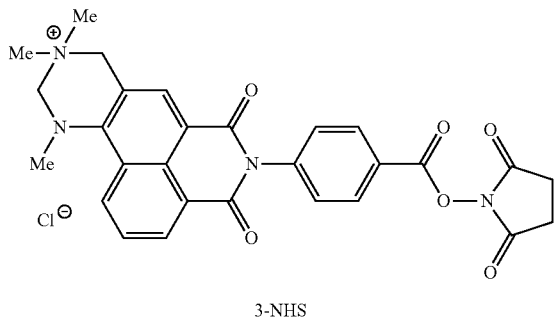

3-NHS 100 mg (0.22 mmol) of 3, 100 mg (0.33 mmol) TSTU, and 76 μL (0.44 mmol) of DIPEA were dissolved in 20 mL of acetonitrile. The obtained solution was stirred at room temperature for 2 h. The reaction was monitored by TLC (RP-18, acetonitrile/water=5/1). After completion, the solvent was removed under reduced pressure and the residue was washed several times with ether, dried and stored in a vacuum desiccator to give NHS ester of 3 with quantitative yield.

Example 13

Covalent Attachment of 3—NHS to BSA

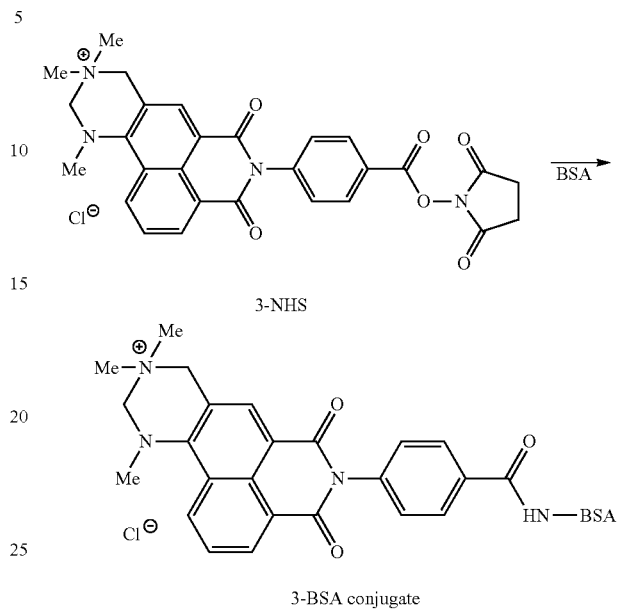

0.8 mg of NHS ester of 3 were dissolved in 80 μL of anhydrous DMF and 17 μL of this solution were added to a solution of 5 mg of BSA in 1 mL of a 50 mM bicarbonate buffer, pH 9.0. The mixture was allowed to stir for 3 h at 25° C. Separation of the dye 3-BSA conjugate from non-conjugated dye was done using a gel permeation chromatography on the 1.5 cm×25 cm column (stationary phase Sephadex G25, eluent 67 mM PB of pH 7.4). The fluorescent fraction of yellow color with the shortest retention time containing the dye-BSA conjugate was collected. The obtained D/P ratio was 3.

Using 60 μL of the above dye-NHS stock solution the dye-BSA conjugate with D/P ratio 8 was obtained.

Example 14 is Compounds of this invention having reactive functionalities other than NHS are described in the literature and can be synthesized according to these procedures. The synthesis of some of these functionalities are described in WO 02/26891 A1.

Maleimides are easily obtain via reaction of the NHS esters with N-(2-aminoethyl)maleimide in an inert solvent.

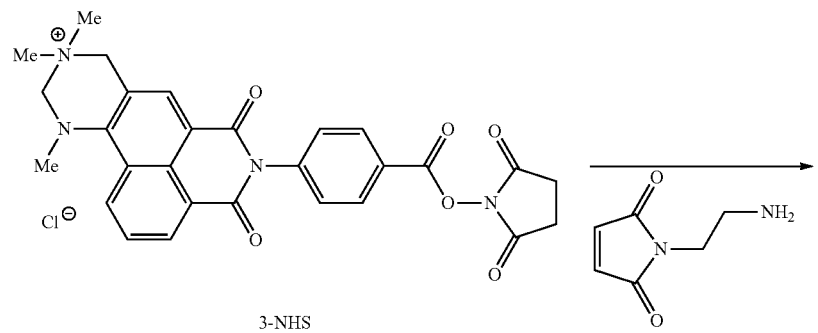

3-NHS

-continued

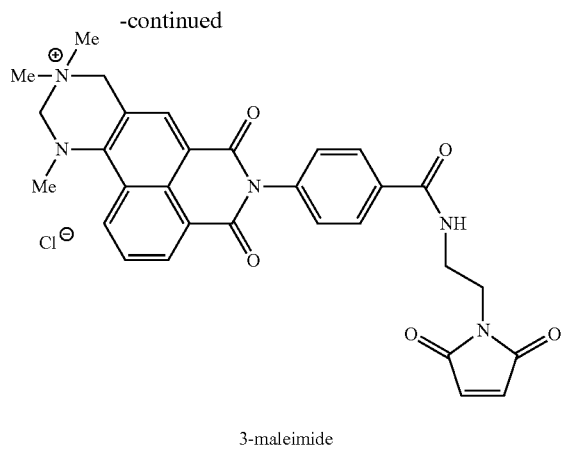

3-maleimide

Spectral Properties of Representative Dyes:

Compounds of this invention have characteristically long lifetimes in the order of 4 ns and above and therefore they are useful in lifetime- and polarization-based assays, Fluorescence Lifetime Imaging (FLIM) and other applications where the luminescence lifetime is the crucial parameter of use. In general the lifetimes of these compounds are between 1 and 30 ns but more typically they are between 5 and 23 ns.

The synthesis of representative dyes is provided in the Examples Section. The structures, absorption and emission data as well as the luminescent lifetime in different solvents of specific dyes are given in Table 1.

In one embodiment of the invention the lifetime probes and labels are based on naphthalic acid derivatives which have lifetimes in the range of 5 to 26 ns or higher. Representative dyes are listed in Table 1 (compounds 3 to 6) and the synthesis of these dyes is described in the Examples Section (Examples 1 to 4). This class of dyes is perfectly suited for excitation with the blue 404 nm or 436 nm diode lasers and some of these compounds were labeled to BSA to demonstrate that these dyes do maintain long lifetimes in presence of proteins. The data in Table 1 also indicate that the luminescent lifetimes of these compounds is not strongly dependent on the solvent system (see compounds 5 and 6). Compound 6 having a long luminescent lifetime of around 23 ns is a potential label for measurement of high-molecular-weight analytes with fluorescence polarization (FIG. 5) that could have wide-spread use for the development of luminescent assays for clinical applications and high-throughput screening.

Reactive derivatives of compound 13 which has a lifetime of 20 ns in water would be very suitable as labels for lifetime based applications.

TABLE 1

Spectral properties and luminescent lifetimes of representative dyes and precursors of this invention

| Dye # | Structure | Solvent | λ(abs) [nm] | λ(fl) [nm] (QY [%]) | Lifetime [ns] |
|---|---|---|---|---|---|
| 3-NHS | 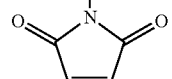  ...—COO—NHS | Water<br>Ethanol | 404<br>390 | 518<br>500 | 9.3<br>8.0 |
| 3a | (structure with —COOH) | Water | 405 | 515<br>(72%) | 9.4 |

TABLE 1-continued
Spectral properties and luminescent lifetimes of representative dyes and precursors of this invention
| Dye # | Structure | Solvent | λ(abs) [nm] | λ(fl) [nm] (QY [%]) | Lifetime [ns] |
|---|---|---|---|---|---|
| 3-IgG | 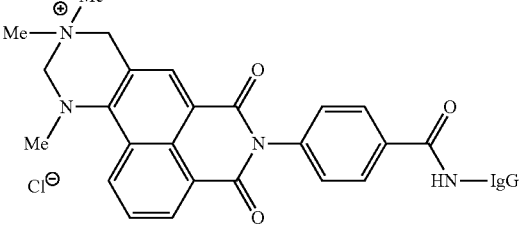 IgG conjugate (D/P = 1) | Water | 405 | 518 | 8.9 |
| 3-IgG | IgG conjugate (D/P ~ 8) | Water | 406 | 518 | 8.4 |
| 4-NHS | 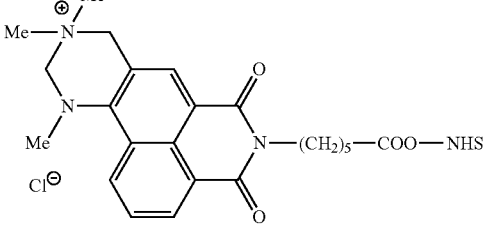 | Water | 402 | 488 | 7.8 |
| 4a-NHS | 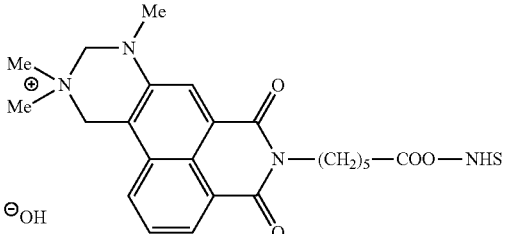 | Water | 425 | 545 (34.5) | 26.1 |
| 5 | 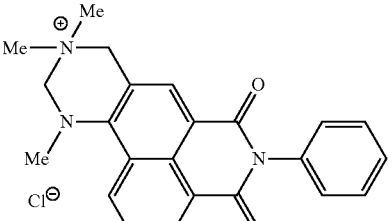 | Water<br>DMF<br>Ethanol | 405<br>393<br>393 | 515<br>(72%)<br>500<br>498<br>(58%) | 9.4<br>9.0<br>8.5 |
| 6 | 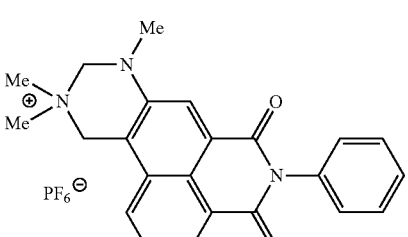 | Ethanol<br>Water | 414<br>426 | 513<br>(51%)<br>545 | 23.3<br>22.9 |

TABLE 1-continued

Spectral properties and luminescent lifetimes of representative dyes and precursors of this invention

| Dye # | Structure | Solvent | λ(abs) [nm] | λ(fl) [nm] (QY [%]) | Lifetime [ns] |
|---|---|---|---|---|---|
| 7b | (structure shown) R = H, Et | Ethanol R = Et | 421 | 492 (59%) | 5.4 |
| 8 | (structure shown) | Ethanol Water Water + BSA | 436 449 449 | 584 (44%) 600 (7%) 600 | 7.8 5.7 6.1 |
| 13 | (structure shown) | Water Ethanol | 398 395 | 481 (40%) 462 (30%) | 20.9 |

Description of Applications of the Invention

The invention relates generally to luminescent compounds containing a benzo-pyrimidinium moiety as a water-soluble functionality having luminescent lifetimes in order of a few ns and higher and their synthetic precursors, and to methods of synthesizing and using such compounds. These luminescent compounds are useful in both their free and conjugated forms, as probes or labels. This usefulness may reflect in part enhancement of one or more of the following: fluorescence lifetime, fluorescence polarization, quantum yield, Stokes' shift, and photostability.

The reporter compounds disclosed above exhibit utility for a variety of useful assay formats.

The assay may be a competitive assay that includes a recognition moiety, a binding partner, and an analyte. Binding partners and analytes may be selected from the group consisting of biomolecules, drugs, and polymers, among others. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

Because of the lifetimes of these labels in the range between 5 and 26 ns, these reagents were found to be in particular useful for fluorescence polarization assays for higher molecular weight analytes (e.g. smaller proteins with a MM of 10 to 40K).

The binding of antagonists to a receptor can be assayed by a competitive binding method in so-called ligand/receptor assays. In such assays, a labeled antagonist competes with an unlabeled ligand for the receptor binding site. One of the binding partners can be, but not necessarily has to be, immobilized. Such assays may also be performed in microplates. Immobilization can be achieved via covalent attachment to the well wall or to the surface of beads.

Other preferred assay formats are immunological assays. There are several such assay formats, including competitive binding assays, in which labeled and unlabeled antigens compete for the binding sites on the surface of an antibody (binding material). Typically, there are incubation times required to provide sufficient time for equilibration.

Such assays can be performed in a heterogeneous or homogeneous fashion. Homonogeneous assays are based on fluorescence polarization or lifetime as the read out parameter (see below).

Sandwich assays may use secondary antibodies and excess binding material may be removed from the analyte by a washing step.

Other types of reactions include binding between avidin and biotin, protein A and immunoglobulins, lectins and sugars (e.g., concanavalin A and glucose).

Due to the presence of the pyrimidinium moiety dyes of this invention are charged (Table 1) and therefore are impermeant to membranes of biological cells. In such cases treatments such as electroporation and shock osmosis can be used to introduce the dye into the cell. Alternatively, such dyes can be physically inserted into the cells by pressure microinjection, scrape loading etc.

The reporter compounds described here also may be used to sequence nucleic acids and peptides. For example, fluorescently-labeled oligonucleotides may be used to trace DNA fragments. Other applications of labeled DNA primers include fluorescence in-situ hybridization methods (FISH) and for single nucleotide polymorphism (SNIPS) applications, among others.

Multicolor labeling experiments may permit different biochemical parameters to be monitored simultaneously. For this purpose, two or more reporter compounds are introduced into the biological system to report on different biochemical functions. The technique can be applied to fluorescence in-situ hybridization (FISH), DNA sequencing, fluorescence microscopy, and flow cytometry among others. One way to achieve multicolor analysis is to label biomolecules such as nucleotides, proteins or DNA primers with different luminescent reporters having distinct luminescence properties (e.g. excitation or emission maxima). Multi-lifetime analysis on the other hand is based on labeling with reporters that have the same excitation and emission maxima but differ due to their distinct luminescence lifetimes. Compounds of this invention have lifetimes in the range from 4 ns to 40 ns and higher and can therefore be easily differentiated by measuring the luminescence lifetime or a relevant parameter (e.g. phase angle).

Phosphoramidites are useful functionalities for the covalent attachment of dyes to oligos in automated oligonucleotide synthesizers. They are easily obtained by reacting the hydroxyalkyl-modified dyes of the invention with 2-cyanoethyl-tetraisopropyl-phosphorodiamidite and 1-H tetrazole in methylene chloride.

The simultaneous use of FISH (fluorescence in-situ hybridization) probes in combination with different fluorophores is useful for the detection of chromosomal translocations, for gene mapping on chromosomes, and for tumor diagnosis, to name only a few applications. One way to achieve simultaneous detection of multiple sequences is to use combinatorial labeling. The second way is to label each nucleic acid probe with a luminophore with distinct properties (e.g lifetime). Conjugates can be synthesized from this invention and can be used in a multicolor-multilifetime multisequence analysis approach.

In another approach the dyes of the invention might be used to directly stain or label a sample so that the sample can be identified and or quantitated. Such dyes might be added/labeled to a target analyte as a tracer. Such tracers could be used e.g. in photodynamic therapy where the labeled compound is irradiated with a light source and thus producing singlet oxygen that helps to destroy tumor cells and diseased tissue samples.

The reporter compounds of the invention can also be used in screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction. It also can be used to detect hybridization or binding of DNA and/or RNA.

Other screening assays are based on compounds that affect the enzyme activity. For such purposes, quenched enzyme substrates of the invention could be used to trace the interaction with the substrate. In this approach, the cleavage of the fluorescent substrate leads to a change in the spectral properties such as the excitation and emission maxima, intensity, polarization and/or lifetime, which allows to distinguish between the free and the bound luminophore.

The dye compounds are also useful for use as biological stains.

Dyes of this invention are also useful for 2-photon experiments. Nonlinear 2-photon excitation is based on the simultaneous absorption of two photons. Since the energy of a photon is inversely proportional to its wavelength, the two absorbed photons must have a wavelength which is about twice that for one-photon excitation. In 2-photon microscopy, two excitation photons from a pulsed laser (Ti:sapphire laser) are combined to excite a fluorescent molecule. The molecule then emits a photon in the visible wavelength. 2-photon microscopy allows for out-of-focus background rejection similar to a confocal microscopy. The advantage of 2-photon microscopy over confocal microscopy is that it can penetrate deeper into tissue due to absence of out-of-focus absorption, the longer excitation wavelength and less scattered light. Nevertheless the achieved optical resolution is the same for both techniques.

Compounds of this invention may also be attached to the surface of metallic nanoparticles such as gold or silver nanoparticles or metal-coated surfaces. It has recently been demonstrated that fluorescent molecules may show increased quantum yields near metallic nanostructures e.g. gold or silver nanoparticles (O. Kulakovich et al. Nanoletters 2 (12) 1449-52, 2002). This enhanced fluorescence may be attributable to the presence of a locally enhanced electromagnetic field around metal nanostructures. The changes in the photophysical properties of a fluorophore in the vicinity of the metal surface may be used to develop novel assays and sensors. In one example the nanoparticle may be labeled with one member of a specific binding pair (antibody, protein, receptor etc) and the complementary member (antigen, ligand) may be labeled with a fluorescent molecule in such a way that the interaction of both binding partners leads to an detectable change in one or more fluorescence properties (such as intensity, polarization, quantum yield, lifetime, phase angle among others). Replacement of the labeled binding partner from the metal surface may lead to a change in fluorescence that can then be used to detect and/or quantify an analyte.

Conventional fluorophores have lifetimes in the range of 100 ps to 4 ns. It is known that the luminescence lifetime of a fluorophore near a metalic nanostructure exhibits shorter lifetimes thus the lifetime of conventional labels will be shortened to an extend that measurement with inexpensive instrumentation is not possible. Dyes of this invention have in average 10 times longer lifetimes than conventional dyes and will therefore allow using inexpensive instrumentation even in presence of metallic nanostructures.

Gold colloids can be synthesized by citrate reduction of a diluted aqueous $HAuCl_4$ solution. These gold nanoparticles are negatively charged due to chemisorption of citrate ions. Surface functionalization may be achieved by reacting the nanoparticles with thiolated linker groups containing amino or carboxy functions. In another approach, thiolated biomolecules are used directly for coupling to these particles.

Analytes

The invention may be used to detect an analyte that interacts with a recognition moiety in a detectable manner. As such, the invention can be attached to a recognition moiety which is known to those of skill in the art. Such recognition moieties allow the detection of specific analytes. Examples are pH-, or potassium sensing molecules, e.g., synthesized by introduction of potassium chelators such as crown-ethers (aza crowns, thia crowns etc). Dyes with N—H substitution in the heterocyclic rings are known to exhibit pH-sensitive absorption and emission (S. Miltsov et al., Tetrahedron Lett. 40: 4067-68, (1999), M. E. Cooper et al., J. Chem. Soc. Chem. Commun. 2000, 2323-2324), Calcium-sensors based on the BAPTA (1,2-Bis(2-aminophenoxy)ethan-N,N,N',N'-tetra-aceticacic) chelating moiety are frequently used to trace intracellular ion concentrations. The combination of a compound of the invention and the calcium-binding moiety BAPTA may lead to new long-wavelength absorbing and emitting Ca-sensors which could be used for determination of intra- and extracellular calcium concentrations (Akkaya et al. Tetrahedron Lett. 38:4513-4516 (1997). Additionally, or in the alternative, reporter compounds already having a plurality of carboxyl functional groups may be directly used for sensing and/or quantifying physiologically and environmentally relevant ions.

Fluorescence Methods

Dyes of this invention are in particular useful for lifetime based applications due to the fact that selected dyes exhibit luminescent lifetimes up to 23 ns and higher (Table 1). The long nanosecond lifetimes of the dyes and dye-protein conjugates may allow the use of relatively inexpensive instrumentation that employs laser diodes for excitation.

Typical assays based on the measurement of the fluorescence lifetime as a parameter include for example FRET (fluorescence resonance energy transfer) assays. The binding between a fluorescent donor labeled species (typically an antigen, or a ligand) and a fluorescent acceptor labeled species may be accompanied by a change in the intensity and/or the fluorescence lifetime. The lifetime can be measured using intensity-(Time corrlated single photon counting TCSPC) or phase-modulation-based methods (J. R. LAKOWICZ, PRINCIPLES OF FLUORESCENCE SPECTROSCOPY ($2^{nd}$ Ed. 1999)). Due to the broad range of lifetimes exhibited by these dyes they can be used simultaneously in multi-lifetime multi-analyte assays (see above).

Figure 4:
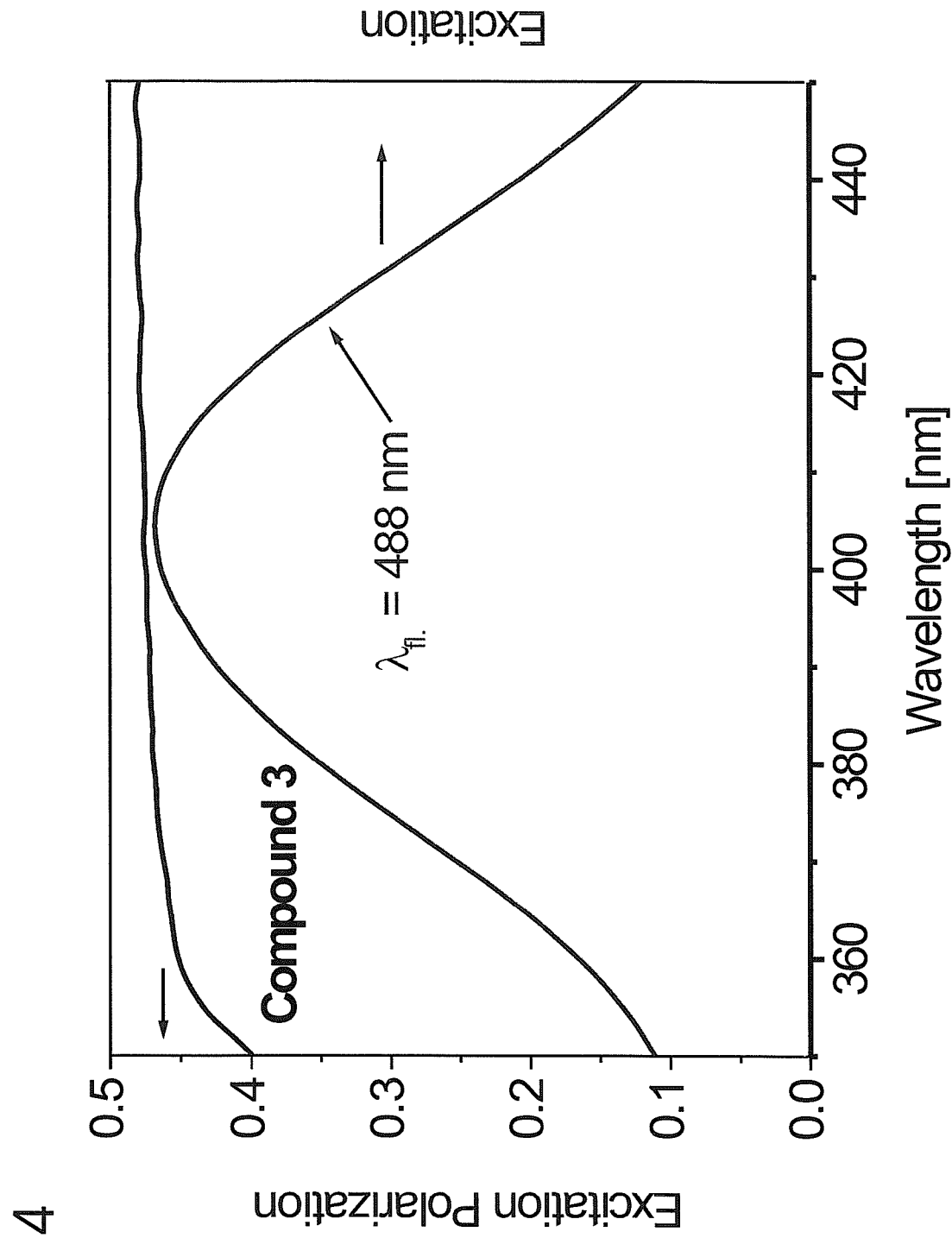
FIG. 4. shows the excitation and excitation polarization spectrum of compound 3 in water FIG. 5. shows the changes in fluorescence polarization of 4a-BSA (MW~65 kDa) upon titration with anti-BSA. Also shown is the data with non-specific antibody. Due to the long lifetime of 4a ($\tau$=26 ns) the fluorescence polarization of 4a-BSA is 165 mP and only upon addition of antibody the polarization increases gradually to its final value of 335 mP. This demonstrates the usefulness of compounds of this invention to measure high-molecular-weight antigens (proteins) in a Fluorescence Polarization Immunoassay (FPA).

Dyes of this invention also exhibit high intrinsic polarization in the absence of rotational motion (FIG. 4), making them useful as tracers in fluorescence polarization (FP) assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration is determined by the change in polarized emission from the fluorescent tracer molecule. The longer luminescent lifetimes of these labels allows the measurement of high molecular weight antigens in a fluorescence polarization assay (FIG. 5) because the MW of the labeled analyte that can be measured in a polarization assay is directly dependent on the luminescence lifetime of the label (E. Terpetschnig et al. Biophys J. 68(1):342-50, 1995).

Compositions and Kits

The invention also provides compositions, kits and integrated systems for practicing the various aspects and embodiments of the invention, including producing the novel compounds and practicing of assays. Such kits and systems may include a reporter compound as described above, and may optionally include one or more of solvents, buffers, calibration standards, enzymes, enzyme substrates, and additional reporter compounds having similar or distinctly different optical properties.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

We claim:

1. A composition of matter comprising a luminescent reporter compound according to the formula:

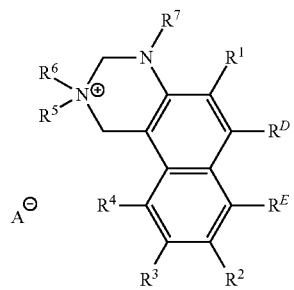

wherein adjacent substituents ($R^D$, $R^E$) together are:

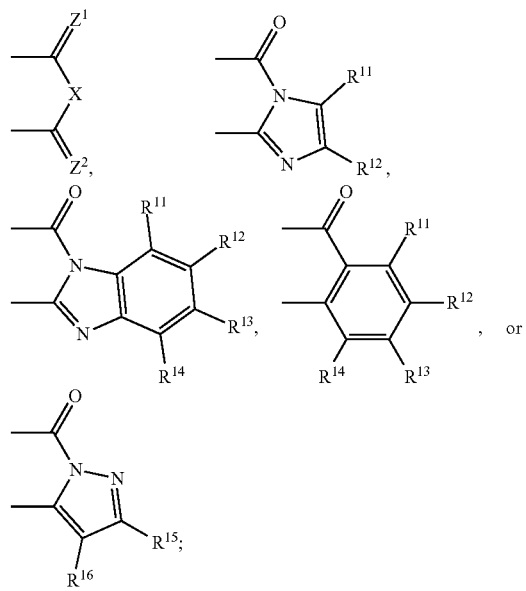

$R^1$-$R^4$ are independently selected from the group consisting of H, -L-$S_c$, -L-$R^x$, -L-$R^±$, alkyl, alkoxy, amino, alkylamino, dialkylamino, alkenyl, alkinyl, aryl, halogen, sulfo, carboxy, formyl, acetyl, formylmethyl, sulfate, phosphate, phosphonate, ammonium, alkylammonium, cyano, nitro, azido, aromatic, heterocyclic, substituted aromatic, substituted heterocyclic, reactive aromatic, and reactive heterocyclic groups;

adjacent substituents ($R^2$, $R^3$), ($R^3$, $R^4$), or ($R^2$, $R^3$, $R^4$) together with interspersed atoms may form aromatic, cyclic or heterocyclic systems that are further substituted with $-L-S_c$, $-L-R^x$, $-L-R^\pm$, aliphatic, cyclic, aromatic, heterocyclic, substituted aromatic and substituted cyclic or heterocyclic groups;

$R^5$-$R^7$ are independently selected from the group consisting of alkyl, aryl, $L-R^x$ and $-L-S_c$; adjacent substituents ($R^5$, $R^6$) may form a cyclic system;

wherein $R^{11}$, $R^{12}$, $R^{13}$, and $R^{14}$, when present, are independently selected from the group consisting of H, $-L-S_c$, $-L-R^x$, $-L-R^\pm$, alkyl, alkoxy, amino, alkylamino, dialkylamino, alkenyl, alkinyl, aryl, halogen, sulfo, carboxy, formyl, acetyl, formylmethyl, sulfate, phosphate, phosphonate, ammonium, alkylammonium, cyano, nitro, and azido;

$R^{15}$ and $R^{16}$ are independently selected from the group consisting of $COOR^A$, alkyl, alkoxy, alkenyl, alkinyl, aryl, alkylaryl, acetyl, cyano, nitro, formyl, halogen, sulfo, sulfate, phosphate, phosphonate, azido, $-L-S_c$, $-L-R^x$, and $-L-R^\pm$;

X is selected from the group consisting of $C(R^B)(R^C)$, O, S, Se, and $N-R^A$;

$Z^1$, $Z^2$ are independently selected from the group consisting of =O, =S, =Se, =Te, =$N-R^A$, and =$C(R^B)(R^C)$;

$R^A$ is selected from the group consisting of H, aliphatic groups, alicyclic groups, alkylaryl groups, aromatic groups, $-L-S_c$, $-L-R^x$, and $-L-R^\pm$;

$R^B$ and $R^C$ are independently selected from the group consisting of H, aliphatic groups, alicyclic groups, alkylaryl groups, aromatic groups, $-L-S_c$, $-L-R^x$, and $-L-R^\pm$; adjacent $R^B$, $R^C$ may form a cyclic group;

L is a covalent linkage that is linear or branched, cyclic or heterocyclic, saturated or unsaturated, having 1-20 non-hydrogen atoms from the group of C, N, P, O, and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;
$S_c$ is a conjugated substance;
$R^\pm$ is an ionic group; and
$A^-$ is any anion.

2. The composition of claim 1, wherein the reporter compound has the formula:

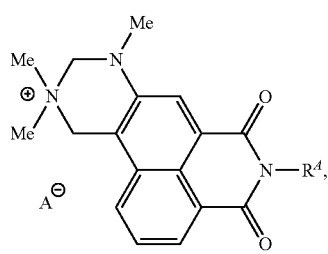

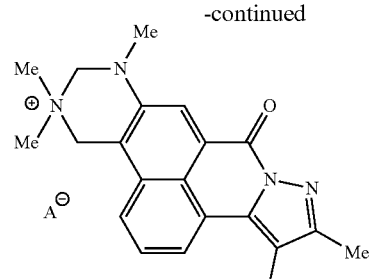

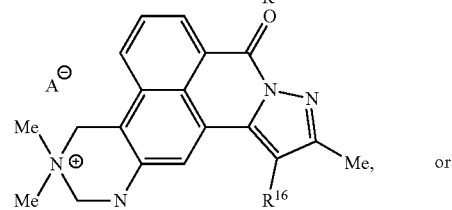

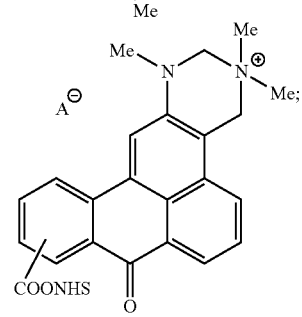

where $R^A$ is selected from the group consisting of H, aliphatic groups, alicyclic groups, alkylaryl groups, aromatic groups, $-L-S_c$, $-L-R^x$, and $-L-R^\pm$;

$R^{16}$ is selected from the group consisting of $COOR^A$, $-L-S_c$, $-L-R^x$, and $-L-R^\pm$; and $A^-$ is any anion.

3. The composition of claim 1, wherein the reactive group $R^x$ is selected from the group consisting of an N-hydroxysuccinimide ester, an isothiocyanate, a sulfonylhalogenide, an anhydride, an iodoacetamide, a maleimide, and a phosphoramidite.

4. The composition of claim 1, wherein the carrier $S_c$ is selected from the group consisting of a protein, DNA, a polypeptide, a polynucleotide, a cell, a carbon nanostructure, a nanoparticle, a metallic nanoparticle, a bead, a microplate well surface, a lipid, a small-molecule drug, a lectin, and a pharmacological agent.

5. The composition of claim 1, further comprising a carrier $S_c$, which is associated covalently with the reporter compound through reaction with a reactive group on at least one substituent.

6. The composition of claim 1, wherein the $R^\pm$ substituent is selected from the group consisting of $-CH_2-CONH-SO_2-Me$, $SO_3^-$, $COO^-$, $PO_3^{2-}$, $O-PO_3^{2-}$, $PO_3R^-$, $O-PO_3R^-$, and $N(R)_3^+$, wherein R are independently an aliphatic or aromatic moiety.

7. The composition of claim 1, wherein the reporter compound is capable of covalently reacting with at least one of biological cells, DNA, lipids, nucleotides, polymers, proteins, lectins, pharmacological agents, and solid surfaces.

8. The composition of claim 1, wherein the reporter compound is covalently or noncovalently associated with at least one of a biological cell, DNA, an oligonucleotide, a lipid, a nucleotide, a polymer, a peptide, a protein, and a pharmacological agent.

9. The composition of claim 1, further comprising a second reporter compound selected from the group consisting of luminophores and chromophores.

10. The composition of claim 9, wherein one of the reporter compound and the second reporter compound is an energy transfer donor and the other of the reporter compound and the second reporter compound is an energy transfer acceptor.

11. A method of performing a photoluminescence assay, the method comprising:
selecting a photoluminescent compound according to claim 1;
exciting the photoluminescent compound with excitation light; and
detecting emission light emitted by the photoluminescent compound.

12. The method of claim 11, further comprising analyzing the emission light to determine at least one of luminescence intensity, luminescence lifetime, a parameter related to luminescence lifetime, and luminescence polarization.

13. The method of claim 11, further comprising performing a luminescence intensity based assay.

14. The method of claim 11, further comprising performing at least one of a luminescence lifetime based assay and a luminescence polarization based assay.

15. The method of claim 11, further performing a fluorescence resonance energy transfer assay.

16. A method of performing a photoluminescence assay, the method comprising:
selecting a photoluminescent compound;
exciting the photoluminescent compound with a burst of excitation light; and
detecting emission light emitted by the photoluminescent compound;
wherein the photoluminescent compound has the formula:

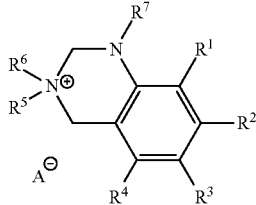

wherein
$R^1$-$R^4$ are independently selected from the group consisting of H, -L-$S_c$, -L-$R^x$, -L-$R^\pm$, alkyl, alkoxy, amino, alkylamino, dialkylamino, alkenyl, alkinyl, aryl, halogen, sulfo, carboxy, formyl, acetyl, formylmethyl, sulfate, phosphate, phosphonate, ammonium, alkylammonium, cyano, nitro, azido, aromatic, heterocyclic, substituted aromatic, substituted heterocyclic, reactive aromatic, and reactive heterocyclic groups,

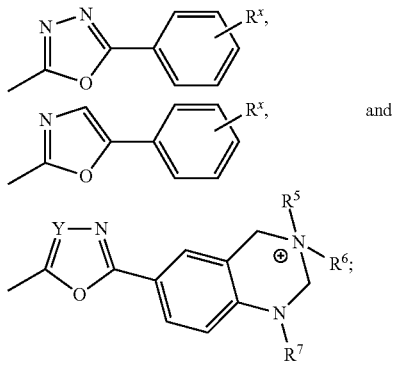

adjacent substituents ($R^1$, $R^2$), ($R^2$, $R^3$), ($R^3$, $R^4$), or ($R^1$, $R^2$, $R^3$) or ($R^2$, $R^3$, $R^4$) together with interspersed atoms may form aromatic, cyclic or heterocyclic systems that are further substituted with -L-$S_c$, -L-$R^x$, -L-$R^\pm$, aliphatic, cyclic, aromatic, heterocyclic, substituted aromatic and substituted cyclic or heterocyclic groups;
$R^5$-$R^7$ are independently selected from the group consisting of alkyl, aryl, L-$R^x$, and -L-$S_c$; adjacent substituents ($R^5$, $R^6$) may form a cyclic system;
L is a covalent linkage that is linear or branched, cyclic or heterocyclic, saturated or unsaturated, having 1-20 non-hydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;
$R^x$ is a reactive group;
$S_c$ is a conjugated substance;
$R^\pm$ is an ionic group;
$A^-$ is any anion;
Y is CH or N;
wherein the photoluminescent compound has a luminescence lifetime of 5 ns or higher, and contains at least one substituent $R^x$ or $S_c$.

17. The method of claim 16, further comprising analyzing the emission light to determine at least one of luminescence intensity, luminescence lifetime, a parameter related to luminescence lifetime, and luminescence polarization.

18. The method of claim 16, further comprising performing a luminescence lifetime based assay.

19. The method of claim 16, further comprising performing a fluorescence resonance energy transfer assay.

20. The method of claim 16, further comprising performing a multi-lifetime assay, wherein a first assay component is labeled with the photoluminescent compound and a second assay component is labeled with a different photoluminescent compound, and wherein the luminescence lifetime of the photoluminescent compound is different than the luminescence lifetime of the different photoluminescent compound.

21. The method of claim 16, further comprising performing a cell-based assay.

22. A method of performing a fluorescence polarization assay for a high molecular weight analyte, the method comprising:
selecting a fluorescent compound;
exciting the fluorescent compound;
detecting polarized emission light emitted by the fluorescent compound; and
determining the fluorescence polarization of the polarized emission light;
wherein the fluorescent compound has the formula:

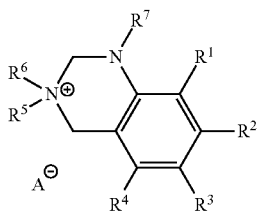

wherein
$R^1$-$R^4$ are independently selected from the group consisting of H, -L-$S_c$, -L-$R^x$, -L-$R^\pm$, alkyl, alkoxy, amino, alkylamino, dialkylamino, alkenyl, alkinyl, aryl, halogen, sulfo, carboxy, formyl, acetyl, formylmethyl, sulfate, phosphate, phosphonate, ammonium, alkylammonium, cyano, nitro, azido, aromatic, heterocyclic, substituted aromatic, substituted heterocyclic, reactive aromatic, and reactive heterocyclic groups,

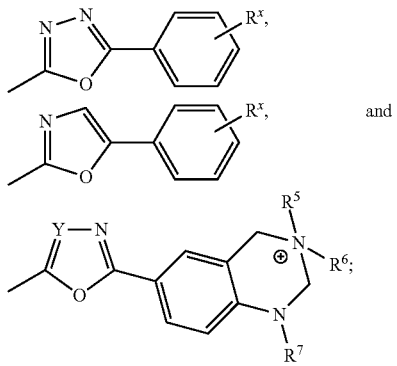

adjacent substituents $(R^1, R^2)$, $(R^2, R^3)$, $(R^3, R^4)$, or $(R^1, R^2, R^3)$ or $(R^2, R^3, R^4)$ together with interspersed atoms may form aromatic, cyclic or heterocyclic systems that are further substituted with $-L-S_c$, $-L-R^x$, $-L-R^\pm$, aliphatic, cyclic, aromatic, heterocyclic, substituted aromatic and substituted cyclic or heterocyclic groups;

$R^5$- $R^7$ are independently selected from the group consisting of alkyl, aryl, L-$R^x$, and -L-$S_c$; adjacent substituents $(R^5, R^6)$ may form a cyclic system;

L is a covalent linkage that is linear or branched, cyclic or heterocyclic, saturated or unsaturated, having 1-20 non-hydrogen atoms from the group of C, N, P, O and S, in such a way that the linkage contains any combination of ether, thioether, amine, ester, amide bonds; single, double, triple or aromatic carbon-carbon bonds; or carbon-sulfur bonds, carbon-nitrogen bonds, phosphorus-sulfur, nitrogen-nitrogen, nitrogen-oxygen or nitrogen-platinum bonds, or aromatic or heteroaromatic bonds;

$R^x$ is a reactive group;

$S_c$ is a conjugated substance;

$R^\pm$ is an ionic group;

$A^-$ is any anion;

Y is CH or N;

wherein the fluorescent compound has a fluorescence lifetime of 5 ns or higher, and contains at least one substituent $R^x$ or $S_c$.

23. The method of claim 22, wherein the high molecular weight analyte has a molecular mass of greater than or equal to 10,000.

24. The method of claim 22, further comprising associating the fluorescent compound with a second molecule.

* * * * *